United States Patent
Lehmann et al.

(10) Patent No.: US 10,576,264 B2
(45) Date of Patent: Mar. 3, 2020

(54) SELECTED SIMULTANEOUS STIMULATION

(71) Applicant: Cochlear Limited, Macquarie University, NSW (AU)

(72) Inventors: Torsten Lehmann, Earlwood (AU); Tony Mikael Nygard, Terrigal (AU)

(73) Assignee: COCHLEAR LIMITED, Macquarie University NSW (AU)

(*) Notice: Subject to any disclaimer, the term of this patent is extended or adjusted under 35 U.S.C. 154(b) by 370 days.

(21) Appl. No.: 15/493,269

(22) Filed: Apr. 21, 2017

(65) Prior Publication Data
US 2018/0304076 A1    Oct. 25, 2018

(51) Int. Cl.
*A61N 1/00* (2006.01)
*A61N 1/02* (2006.01)

(52) U.S. Cl.
CPC .................................. *A61N 1/025* (2013.01)

(58) Field of Classification Search
CPC .......................... A61N 1/025; A61N 1/36038
See application file for complete search history.

(56) References Cited

U.S. PATENT DOCUMENTS

| | | | |
|---|---|---|---|
| 9,037,249 B2* | 5/2015 | Parramon | A61N 1/0551 607/46 |
| 9,314,617 B2 | 4/2016 | He et al. | |
| 2007/0179565 A1 | 8/2007 | Overstreet et al. | |
| 2008/0021520 A1 | 1/2008 | Dietrich | |
| 2009/0216296 A1 | 8/2009 | Meskens | |
| 2011/0125217 A1 | 5/2011 | Carter et al. | |
| 2012/0083859 A1 | 4/2012 | Sun et al. | |
| 2012/0109256 A1 | 5/2012 | Meskins et al. | |
| 2013/0006315 A1* | 1/2013 | Lee | A61N 1/36125 607/2 |

FOREIGN PATENT DOCUMENTS

KR    10-2010-0068383    6/2010

OTHER PUBLICATIONS

International Search Report and Written Opinion in corresponding International Application No. PCT/IB2018/052627, dated Aug. 17, 2018, 8 pages.

* cited by examiner

*Primary Examiner* — Mallika D Fairchild
(74) *Attorney, Agent, or Firm* — Edell, Shapiro & Finnan, LLC

(57) ABSTRACT

Presented herein are implantable medical devices, such as tissue-stimulating prostheses, that are configured to deliver simultaneous stimulation to a recipient. In one embodiment, a tissue stimulating prosthesis comprises a plurality of current sources, a plurality of electrodes (e.g., a linear array of electrodes), and a hardwired electrical network of switches, sometimes referred to herein as a "sparse switch network." The sparse switch network is configured to connect each of the current sources to more than one of the electrodes, and to connect each of the electrodes to only a subset of the current sources. The sparse switch network is configured to prevent adjacent electrodes from being connected to the same current source.

23 Claims, 16 Drawing Sheets

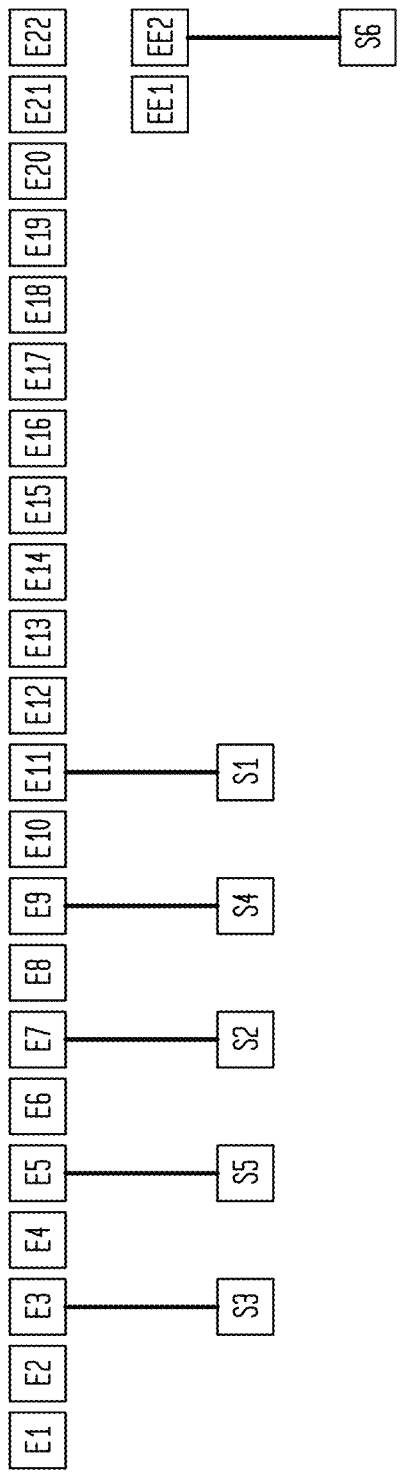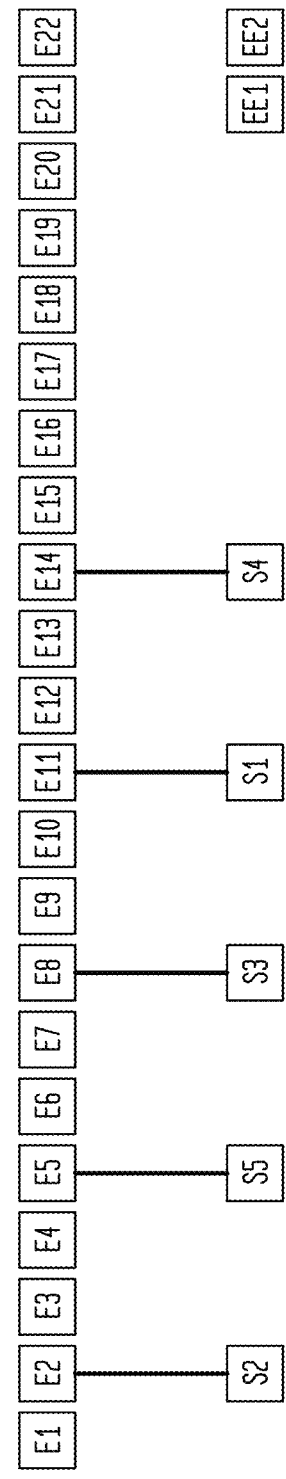
FIG. 4C
FIG. 4D

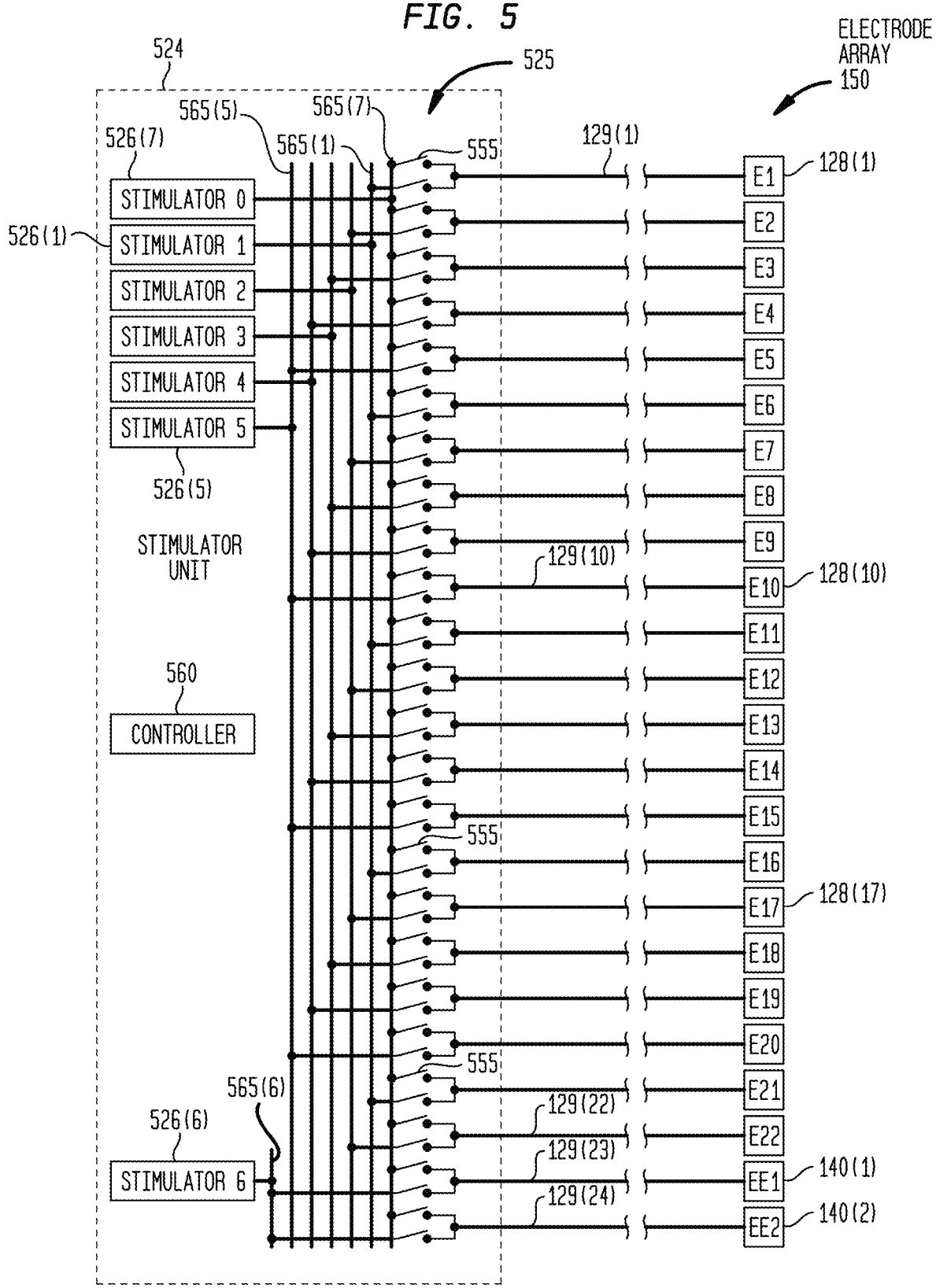

SELECTED SIMULTANEOUS STIMULATION

BACKGROUND

Field of the Invention

The present invention relates generally to tissue-stimulating prostheses.

Related Art

There are several types of implantable medical devices that operate by delivering electrical (current) stimulation to the nerves, muscle or other tissue fibers of a recipient. These medical devices, sometimes referred to herein as tissue-stimulating prostheses, typically deliver stimulation signals (current) to compensate for a deficiency in the recipient. For example, tissue-stimulating hearing prostheses, such as cochlear implants, are often proposed when a recipient experiences sensorineural hearing loss due to the absence or destruction of the cochlear hair cells, which transduce acoustic signals into nerve impulses. Auditory brainstem stimulators are another type of tissue-stimulating hearing prostheses that might be proposed when a recipient experiences sensorineural hearing loss due to damage to the auditory nerve.

SUMMARY

In one aspect presented herein, an implantable medical device is provided. The implantable medical device comprises: current sources configured to generate stimulation signals for delivery to a recipient of the implantable medical device; an array of stimulating electrodes; and a plurality of switches configured to selectively electrically connect each of a plurality of the current sources to a plurality of the stimulating electrodes, wherein the plurality of switches is arranged to prevent adjacent stimulating electrodes from being connected to the same one of the plurality of current sources.

In another aspect presented herein, a tissue-stimulating prosthesis is provided. The tissue-stimulating prosthesis system comprises: a plurality of electrodes; a plurality of current sources; and a sparse switch network configured to: (i) connect each of the current sources to more than one of the electrodes, and (ii) connect each of the electrodes to only a subset of the current sources.

In another aspect presented herein, a tissue-stimulating prosthesis is provided. The tissue-stimulating prosthesis system comprises: a plurality of current sources, wherein each of the current sources is configured to produce an electrical stimulation signal; an array of stimulating electrodes, wherein the electrodes are configured to deliver electrical stimulation signals received from the current sources to tissue of a recipient; and a hardwired electrical network that connects each of the current sources to only a subset of the electrodes.

BRIEF DESCRIPTION OF THE DRAWINGS

Embodiments of the present invention are described herein in conjunction with the accompanying drawings, in which:

FIGS. 4A, 4B, 4C, 4D, and 4E are diagrams illustrating different example stimulation patterns facilitated/enabled by sparse switch network, in accordance with embodiments presented herein;

FIG. 5 is a schematic diagram illustrating another stimulator unit having a sparse switch network, in accordance with embodiments presented herein;

DETAILED DESCRIPTION

Presented herein are implantable medical devices, such as tissue-stimulating prostheses, that are configured to deliver simultaneous stimulation to a recipient. In one embodiment, a tissue stimulating prosthesis comprises a plurality of current sources, a plurality of electrodes (e.g., a linear array of electrodes), and a hardwired electrical network of switches, sometimes referred to herein as a "sparse switch network." The sparse switch network is configured to connect each of the current sources to more than one of the electrodes, and to connect each of the electrodes to only a subset of the current sources. The sparse switch network is configured to prevent adjacent electrodes from being connected to the same current source.

There are a number of different types of tissue-stimulating prostheses that deliver stimulation signals (current) to a recipient (e.g., to compensate for a deficiency in a recipient). Merely for ease of illustration, the embodiments presented herein are primarily described herein with reference to one type of tissue-stimulating prosthesis, namely a cochlear implant. It is to be appreciated that the techniques presented herein may be used with other tissue-stimulating prostheses including, for example, auditory brainstem stimulators, implantable pacemakers, defibrillators, deep brain stimulations, functional electrical stimulation devices, pain relief stimulators, visual prostheses, other neural or neuromuscular stimulators, etc.

Figure 1A:
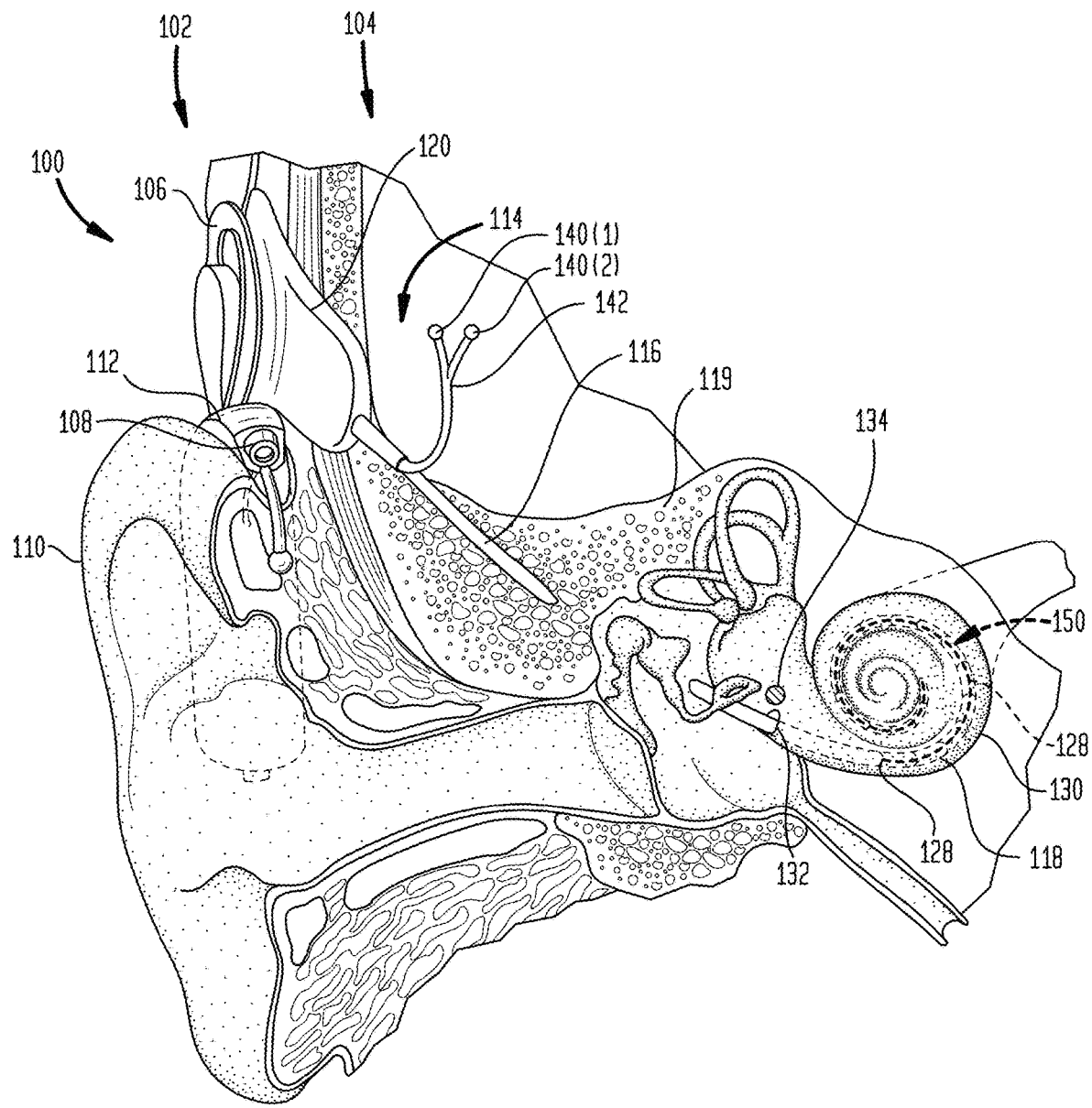
FIG. 1A is a schematic diagram illustrating a cochlear implant, in accordance with embodiments presented herein.
Figure 1B:
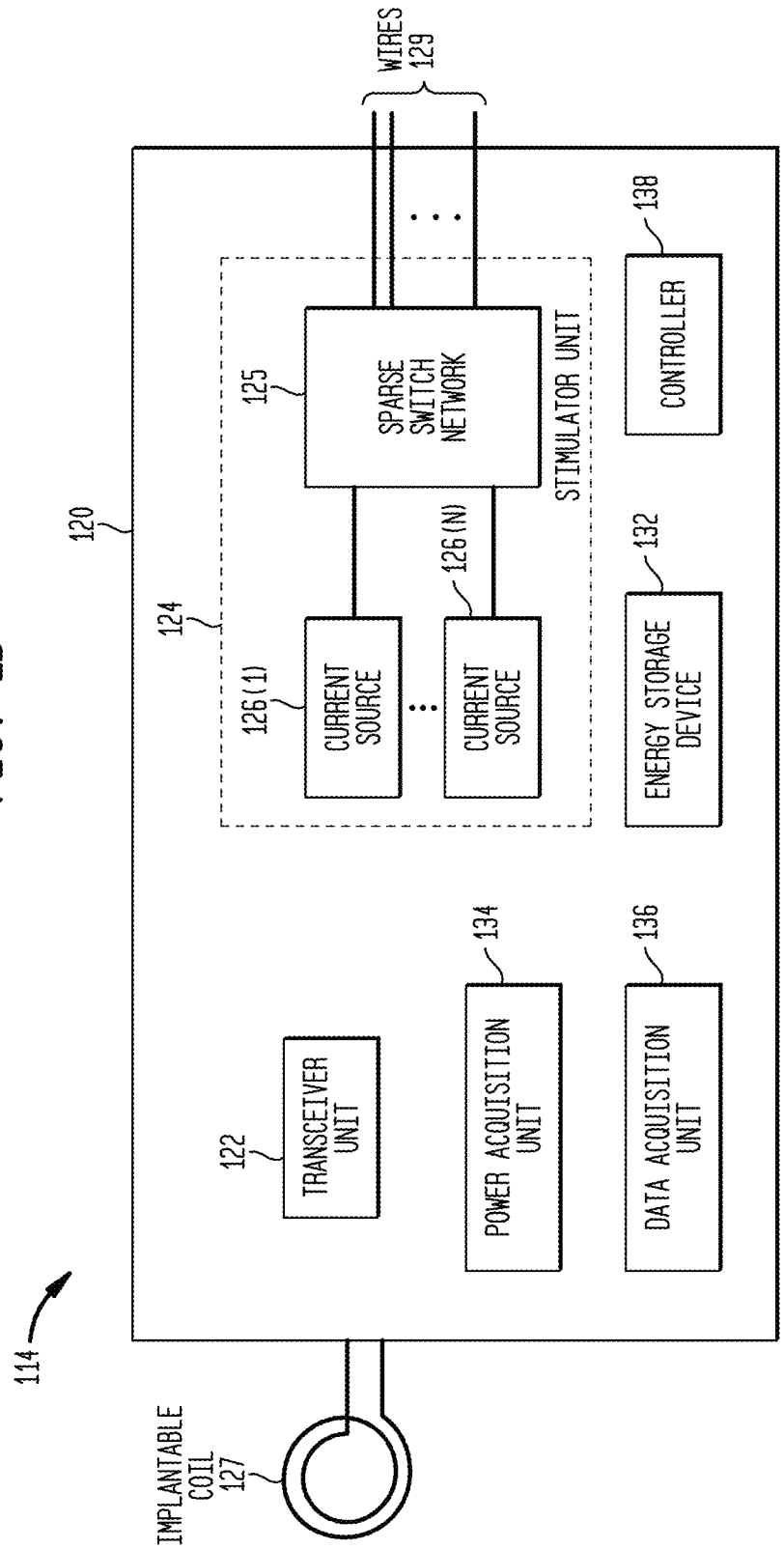
FIG. 1B is a block diagram illustrating further details of the cochlear implant of FIG. 1A.

FIG. 1A is schematic diagram of an exemplary cochlear implant system 100 configured to implement embodiments of the present invention. The cochlear implant system 100 comprises an external component 102 and an internal/implantable component 104. In this example, the implantable component 104 is a cochlear implant. FIG. 1B is a schematic diagram of a portion of cochlear implant 104.

The external component 102 is directly or indirectly attached to the body of the recipient and typically comprises an external coil 106 and, generally, a magnet (not shown in FIG. 1A) fixed relative to the external coil 106. The external component 102 also comprises one or more sound input elements 108 (e.g., microphones, telecoils, etc.) for detecting/receiving sound signals, and a sound processing unit 112. The sound processing unit 112 includes, for example, a power source (not shown in FIG. 1A) and a sound processor (also not shown in FIG. 1A). The sound processor is configured to process electrical signals generated by a sound input element 108 that is positioned, in the depicted embodiment, by auricle 110 of the recipient. The sound processor provides the processed signals to external coil 106 via, for example, a cable (not shown in FIG. 1A).

The cochlear implant 104 comprises an implantable main module (implant body) 114, a lead region 116, and an elongate intra-cochlear stimulating assembly 118. As shown in FIG. 1B, the main module 114 comprises a hermetically sealed housing 120 in which an internal receiver/transceiver unit 122, sometimes referred to herein as receiver/transceiver circuitry or a transceiver unit, and a stimulator unit 124 are disposed. The stimulator unit 124 comprises a plurality of current sources (stimulators) 126(1)-126(N) configured to generate stimulation signals (current) for delivery to the recipient. As shown, the stimulator unit 124 also comprises a hardwired electrical network of switching elements (switches), sometimes referred to herein as a "sparse switch network" 125.

The physical arrangement/implementation of current sources, such as current sources 126(1)-126(N), are typically done on a monolithic integrated circuit (IC) to meet implant volume needs and power restrictions and takes significant resources. Some features for the current sources are high resolution, low power dissipation, high voltage compliance, and fast operation. These features need to be traded off against one other and against the physical layout area (e.g., IC chip area) and/or volume available for the current sources and associated switching arrangements. One particular limiting factor in contemporary IC technologies is the high compliance (e.g., 5V-20V) current electrode technologies impose on the system. IC devices that can sustain such high voltages require special manufacturing steps and make the devices physically large.

The transceiver unit 122 is connected to an implantable coil 127 (FIG. 1B) and, generally, a magnet (not shown) is fixed relative to the implantable coil 127. The magnets in the external component 102 and cochlear implant 104 facilitate the operational alignment of the external coil 106 with the implantable coil 127. The operational alignment of the coils enables the implantable coil 127 to receive power and data from, and possibly send data to, the external coil 106. More specifically, in certain examples, external coil 106 transmits electrical signals (e.g., power and stimulation data) to implantable coil 127 via a closely-coupled link. Implantable coil 127 is typically a wire antenna coil comprised of multiple turns of electrically insulated single-strand or multi-strand platinum or gold wire. The electrical insulation of implantable coil 127 is provided by a flexible molding (e.g., silicone molding). It is to be appreciated that various types of transfer methods, such as infrared (IR), electromagnetic, capacitive transfer, inductive transfer, etc. may be used to transfer the power from an external device to a cochlear implant and to transfer data between an external device and a cochlear implant. As such, FIGS. 1A and 1B illustrate only one example arrangement for transfer of power and/or date to the cochlear implant 104.

Elongate stimulating assembly 118 is configured to be at least partially implanted in cochlea 130 and includes a plurality of longitudinally spaced intra-cochlear electrodes 128. Stimulating assembly 118 extends through an opening in the cochlea 130 (e.g., cochleostomy 132, the round window 134, etc.) and has a proximal end connected to stimulator unit 124 via the sparse switch network 125 and lead region 116 that extends through mastoid bone 119.

Also shown in FIG. 1A are two extra-cochlear electrodes 140(1) and 140(2) that are positioned outside of (external to) the recipient's cochlea. A reference lead region 142, which comprises one or more wires or leads embedded in an electrically-insulating material, electrically connects the extra-cochlear electrodes 140(1) and 140(2) to the sparse switch network 125. As described further below, the extra-cochlear electrodes 140(1) and 140(2) may, in certain arrangements, operate as counter electrodes when delivering stimulation current via one or more of the intra-cochlear electrodes 128(1)-128(22). The intra-cochlear electrodes 128(1)-128(22) and the extra-cochlear electrodes 140(1) and 140(2) are sometimes generally and collectively referred to herein using the term "implant electrodes." However, the terms "stimulating electrodes" or "primary electrodes" are sometimes used herein to refer to the intra-cochlear electrodes 128(1)-128(22) separately from the extra-cochlear electrodes 140(1) and 140(2), since the intra-cochlear electrodes are positioned proximate to the target nerve cells (i.e., the nerve cells to be stimulated). In contrast, the extra-cochlear electrodes 140(1) and 140(2) are "reference electrodes" that supplement operation of the stimulating/primary electrodes (i.e., the intra-cochlear electrodes). It is to be appreciated that the terms "stimulating electrodes" or "primary electrodes" herein generally refer to groups of electrodes that are positioned proximate to target nerve cells and operate as the primary source of stimulation to the recipient, while excluding electrodes that are positioned farther from the target nerve cells.

Figure 1C:
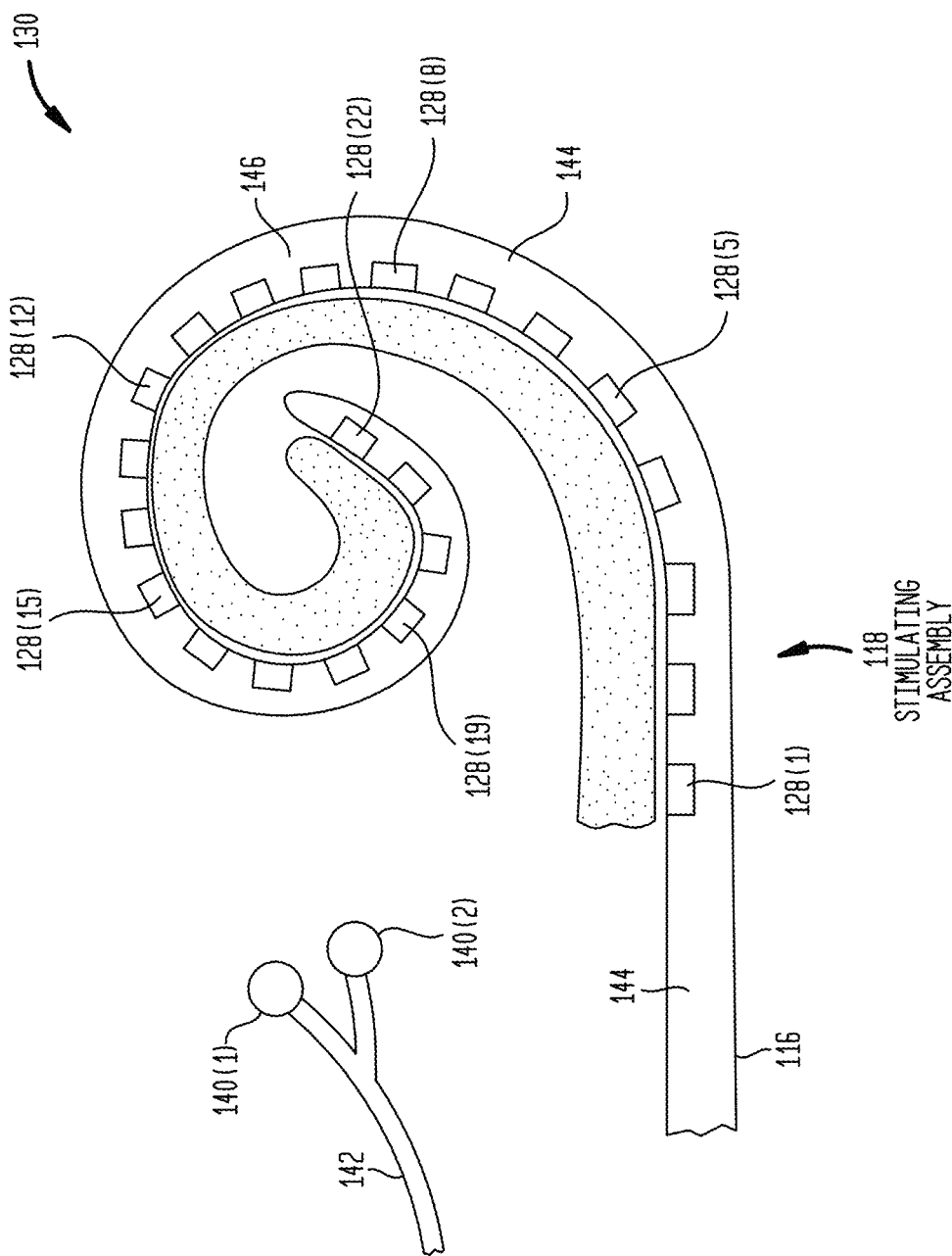
FIG. 1C is a schematic diagram illustrating further details of the cochlear implant of FIG. 1A.

FIG. 1C is a schematic diagram providing a more detailed view of the stimulating assembly 118 of FIG. 1A when implanted in cochlea 130. FIG. 1C illustrates a specific arrangement in which stimulating assembly 118 comprises twenty-two (22) electrodes 128, labeled in FIG. 1C as electrodes 128(1) through 128(22). The electrodes 128(1)-128(22) form an electrode array 150. However, it is to be appreciated that embodiments presented herein may be implemented in alternative arrangements having different numbers of electrodes.

As shown, electrode 128(1) is the most basal/proximal electrode, while electrode device 128(22) is the most distal/apical electrode. The electrodes 128(1)-128(22) are each disposed in an electrically-insulating body 144 formed, for example, from an elastomer or other resiliently flexible material. The electrodes 128(1)-128(22) are all connected to the sparse switch network 125 via wires 129 (FIG. 1B) that extend through the body 144 of the stimulating assembly 118 and the lead region 116 (not shown in FIG. 1B or 1C). For ease of illustration, these wires 129 have been omitted from FIG. 1C. FIG. 1C also illustrates the extra-cochlear electrodes 140(1) and 140(2) positioned outside of the recipient's cochlea and a portion of the reference lead region 142.

Returning to FIG. 1B, the main module 114 further includes an energy storage device 132 (e.g., an implanted battery or a short-term energy storing capacitor), a power management unit 134, a data acquisition unit 136, and a controller (control unit) 138. The power management unit 134 is configured to supply, using the energy storage device 132, a suitable stimulation power (VDD) to the stimulator unit 124. As noted above, the transceiver 122 is configured to enable communication with other parts of the cochlear implant system 100 (e.g., via implantable coil 127). The data acquisition unit 136 is configured to acquire data, such as electrode voltages, neural response signals, implant health and diagnostic signals, etc. The controller 138 is configured to control the operations of the various other components of the main module 114. For ease of illustration, connections between the various components of the main module 114 have been omitted from FIG. 1B. It is also to be appreciated that the main module 114 may include other elements, such as test interfaces, diagnostic functionality, etc., as would be understood by a person skilled in the art. For ease of illustration, these various other elements, which are not relevant to the present disclosure, have been omitted from FIG. 1B.

As noted, the main module 114 also comprises the stimulator unit 124 which, as noted above, comprises the plurality of current sources 126(1)-126(N) and the sparse switch network 125. As used herein, a "current source" comprises one or more electronic circuit elements that deliver (source) and/or absorb (sink) an electric current. Also as used herein, the terms "sinking" and "sourcing" are terms used to define the direction of current flow in a recipient's tissue. A current source that is "sourcing" (i.e., sources/delivers current) provides a current flowing into the recipient's tissue (i.e., the load). A current source that is "sinking" (i.e., sinks/absorbs current) provides a current flowing out of the recipient's tissue. As such, the terms "current source" or "stimulator" are to be broadly construed to include any element that can source current, sink current, or both source and sink current.

As described further below, the sparse switch network 125 is configured to, at different times, selectively connect each of the current sources 126(1)-126(N) to only a subset of the implant electrodes (i.e., intra-cochlear electrodes 128(1)-128(22) and the extra-cochlear electrodes 140(1) and 140(2)). That is, as described further below, the sparse switch network 125 comprises a limited/constrained number of switching elements (switches) that are arranged so as to, at given times, connect each of the current sources in the stimulator unit 124 to only a limited number of the implant electrodes. In certain embodiments, the switches in the sparse switch network 125 are arranged to prevent adjacent intra-cochlear electrodes from being connected to the same current source. Alternatively or additionally, the sparse switch network 125 can be configured to connect, at different times, each of the current sources 126(1)-126(N) to more than one of the implant electrodes. In addition, the sparse switch network 125 can be configured to connect each of the implant electrodes to only a subset of the current sources.

FIGS. 1A-1C illustrate an arrangement in which the cochlear implant system 100 includes an external component. However, it is to be appreciated that embodiments of the present invention may be implemented in cochlear implant systems, or other prosthesis systems, having alternative arrangements. For example, embodiments of the present invention can also be implemented in a totally implantable cochlear implant, or another type of totally implantable tissue-stimulating prosthesis. In a totally implantable prosthesis, all components are configured to be implanted under skin/tissue of a recipient and, as such, the prosthesis operates for at least a finite period of time without the need of an external device.

It is also to be appreciated that FIGS. 1A, 1B, and 1C only illustrate certain components of the cochlear implant system 100. As such, it is to be appreciated that the example of FIGS. 1A, 1B, and 1C is illustrative and that cochlear implant systems in accordance with embodiments presented herein may include other components or elements that are not shown in FIG. 1A, 1B, or 1C.

Traditionally, cochlear implants have used sequential monopolar stimulation to evoke hearing percepts. In sequential monopolar stimulation, an intra-cochlear electrode is used to source stimulation signals (current) and an extra-cochlear electrode is used to sink the stimulation signals. In addition, only one electrode at a time is used to deliver the stimulation signals to the recipient and a number of different electrodes may be used in a predetermined sequence. Cochlear implants that deliver sequential monopolar stimulation typically utilize one current source that is selectively connectable to any of the intra-cochlear electrodes in order to deliver the stimulation signals via any of the electrodes. Another current source may be selectively connected to an extra-cochlear electrode in order to sink the stimulation signals.

Ideally, it is desirable for stimulation signals to stimulate only a narrow region of a recipient's cochlea (i.e., a narrow region of spiral ganglion neurons) such that the resulting neural responses from neighboring stimulation channels have minimal overlap. However, monopolar stimulation typically exhibit a high degree of overlap such that a target neuron population may be excited by several different monopolar channels (i.e., monopolar stimulation delivered at different intra-cochlear electrodes). As such, other types of stimulation strategies, including bipolar, tripolar, focused multi-polar ((FMP), a.k.a. "phased-array") stimulation, etc., generally and collectively referred to herein as "focused stimulation strategies" or "focused stimulation" have been developed in an attempt to reduce the size of an excited neural population. These focused stimulation strategies generally employ some form of simultaneous stimulation in which stimulation signals are delivered via multiple different electrodes at substantially the same time using different magnitudes and different polarities (i.e., different current directions) in order to precisely control the current flow in the recipient's tissue.

Figure 2:
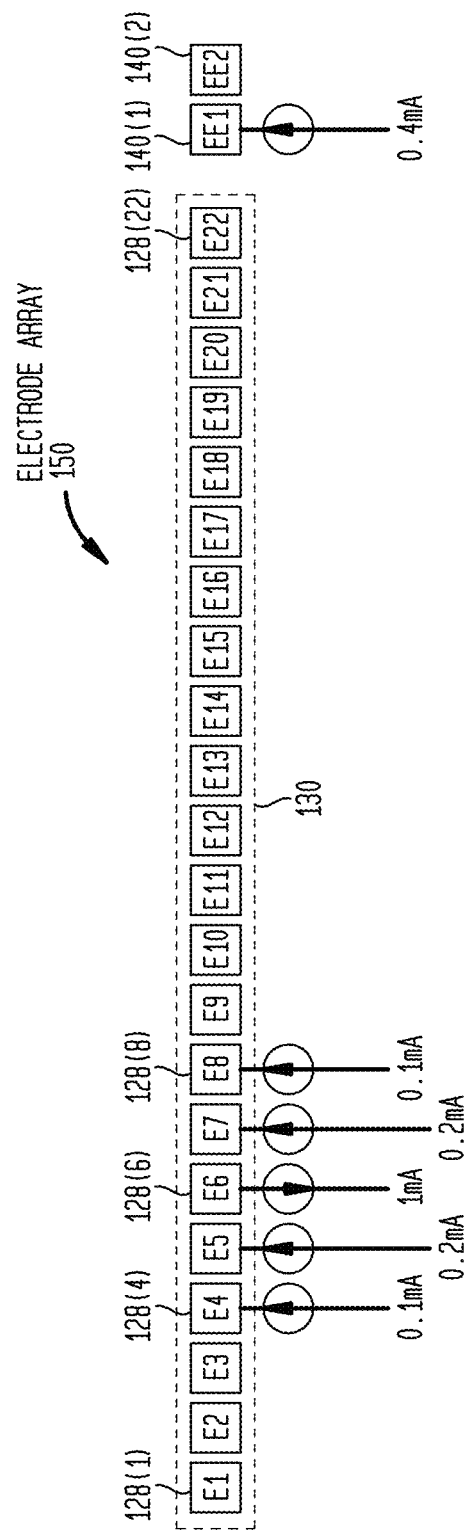
FIG. 2 is schematic diagram illustrating delivery of simultaneous stimulation via an electrode array, in accordance with embodiments presented herein.

FIG. 2 is a schematic diagram illustrating the delivery of focused stimulation via the stimulating assembly 118 of FIGS. 1A-1C. As noted, the intra-cochlear electrodes 128(1)-128(22) comprise a linear electrode array 150 positioned inside the cochlea, while the extra-cochlear electrodes 140(1) and 140(2) are positioned outside the cochlea.

In the example of FIG. 2, a group of consecutive intra-cochlear electrodes, namely intra-cochlear electrodes 128(4)-128(8), are used to simultaneously source or sink current (i.e., deliver current at different magnitudes and different polarities/directions) in order to precisely control the current flow in the tissue. More specifically, electrodes 128(4) and 128(8) source (i.e., deliver positive polarity current) 0.1 mA of current, electrodes 128(5) and 128(7) source 0.2 mA of current, and electrode 128(6) sinks 1 mA of current. In addition, in this example, extra-cochlear electrode 140(1) is also used to source an additional 0.4 mA of current. In other words, FIG. 2 illustrates an arrangement where an extra cochlear electrode (EE1) is used in addition to the intra-cochlear electrodes (E4-E8). As described further below, the focused stimulation shown in FIG. 2 can be produced by the sparse switch network 125 (FIG. 1B) which is configured to, at different times, selectively connect each of the current sources current sources 126(1)-126(N) in the stimulator unit 124 to only a subset of the electrodes 128(1) through 128(22) and/or to the extra-cochlear electrodes 140(1) and 140(2).

Focused stimulation (and other simultaneous stimulation where stimulation signals are delivered via multiple intra-cochlear electrodes at the same time), such as that shown in FIG. 2, generally offers better concentration of the stimulation current flow at the intended excitable tissue, relative to monopolar stimulation strategies, with the potential for better hearing outcomes in cochlear implant recipients.

For complete flexibility in the stimulation current profile (i.e., how the stimulation signals are delivered), each intra-cochlear electrode can have a dedicated current source controlling the current delivered via that specific electrode (i.e., a one-to-one correspondence between current sources and intra-cochlear electrodes). Another option is to link each current source to all of the electrodes via a conventional complete/full switch matrix (a matrix of switches capable of switching any current source to any electrode) to achieve similar flexibility.

The inventors of the present application have recognized that, in many simultaneous stimulation strategies, it is not necessary to stimulate via all intra-cochlear electrodes at the same time. Instead, the inventors have recognized that it is sufficient to simultaneously stimulate via only on a subset of the intra-cochlear electrodes at an instance in time and, as result, a one-to-one correspondence between current sources and intra-cochlear electrodes is unnecessary to provide a useful system with simultaneous stimulation capabilities. The inventors have also recognized that most useful simultaneous stimulation strategies exhibit electrode patterns that don't require full interconnectivity between each current source and all the electrodes (e.g. as provided by a conventional full switch matrix). Accordingly, presented herein are new arrangements for cochlear implants or other tissue-stimulating prostheses that enable the prosthesis to provide simultaneous stimulation to a recipient, but do so with limited numbers of current sources and switches.

Figure 3:
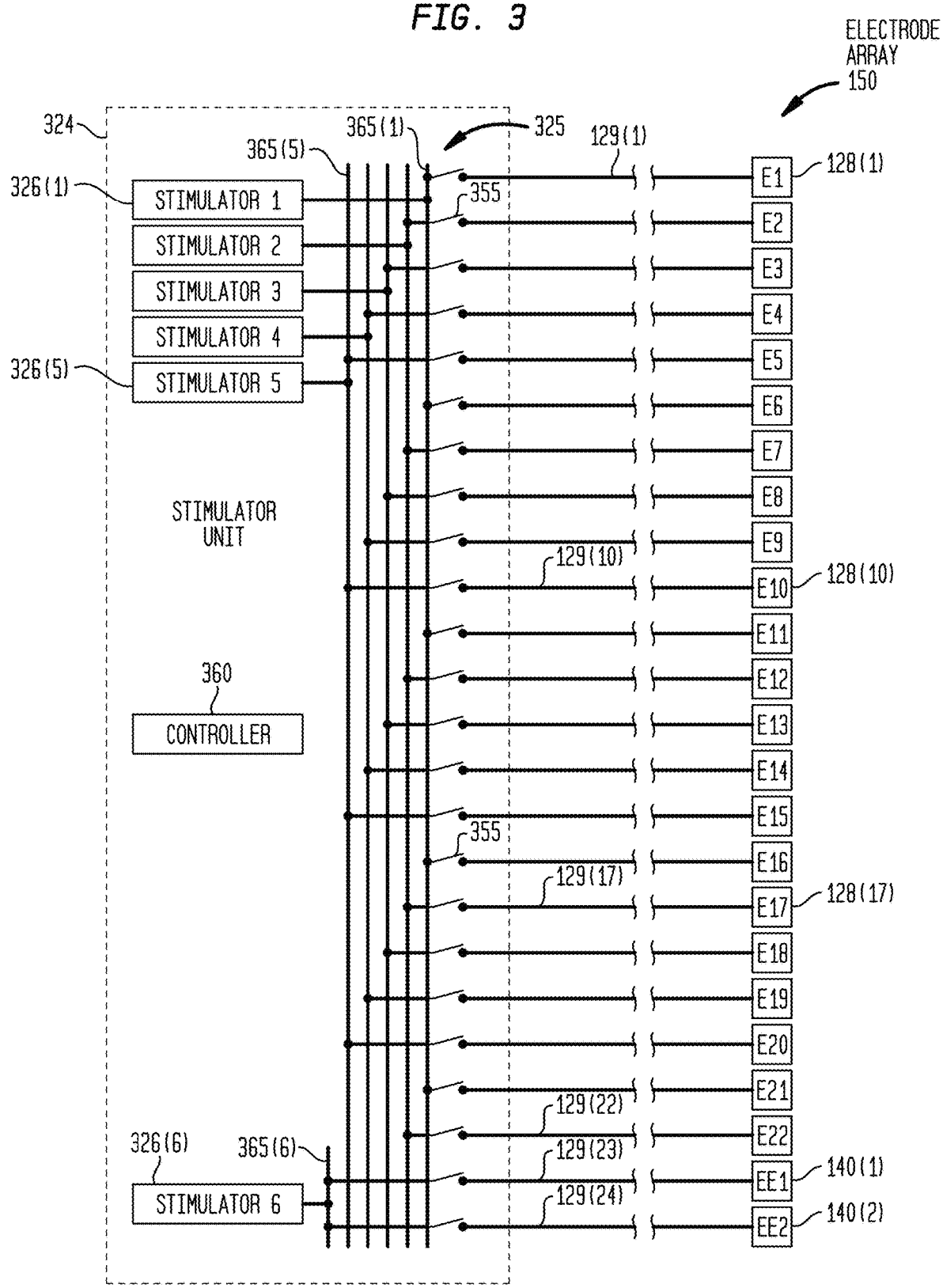
FIG. 3 is a schematic diagram illustrating a stimulator unit having a sparse switch network, in accordance with embodiments presented herein.

For example, FIG. 3 is a schematic diagram illustrating one embodiment of stimulator unit 124, referred to herein as stimulator unit 324, in accordance with embodiments presented herein. In this embodiment, the stimulator unit 324 comprises six current sources (stimulators) 326(1)-326(6) and a sparse switch network 325. The sparse switch network 325 is formed by a plurality of switching elements (switches) 355 that operate under the control of a control unit (controller) 360. For ease of illustration, connections between the switches 355 and the controller 360 have been omitted from FIG. 3. Although FIG. 3 illustrates the presence of a controller 360 that forms part of stimulator unit 324, it is to be appreciated that this is merely illustrative and that switches 355 may be controlled/actuated by a separate controller, such as an implant controller (e.g., controller 138 in FIG. 1B).

The stimulator unit 324 is shown with the extra-cochlear electrodes 140(1) and 140(2), as well as the electrode array 150 of FIGS. 1A-1C and 2. Each of the intra-cochlear electrodes 128(1)-128(22) in the electrode array 150 are electrically connected to the sparse switch network 325 via a corresponding wire 129(1)-129(22). Similarly, the extra-cochlear electrodes 140(1) and 140(2) are connected to the sparse switch network 325 via wires 129(23) and 129(24), respectively.

In accordance with embodiments presented herein, the sparse switch network 325 is configured to selectively connect each of the current sources 326(1)-326(5) to a plurality (i.e., more than one) of the intra-cochlear electrodes 128(1)-128(22) at different times, and to selectively connect each of the intra-cochlear electrodes 128(1)-128(22) to only a subset of the current sources 326(1)-326(5). In addition, the sparse switch network 325 is configured to selectively connect the current source 326(6) to the extra-cochlear electrode 140(1) and/or the extra-cochlear electrode 140(2). In other words, the sparse switch network 325 is a hardwired electrical network comprised of a plurality of switches 355 that is configured to selectively connect, at different times, each of the current sources 326(1)-326(6) to only a subset of the implanted electrodes (i.e., electrodes 128(1)-128(22), 140(1), or 140(2)). The plurality of switches 355 are arranged to prevent adjacent intra-cochlear electrodes 128(1)-128(22) from being connected to the same current source 326(1)-326(5). When connected to an electrode, the current sources 326(1)-326(6) may each source or sink current.

As shown in FIG. 3, each of the current sources 326(1)-326(6) is connected to a corresponding distribution line 365(1)-365(6). In certain embodiments, the sparse switch network 325 is arranged such that each intra-cochlear electrode 128(1)-128(22) can be switched to one and only one of the distribution lines 365(1)-365(5), while the extra-cochlear electrodes 140(1) and 140(2) can each be connected to the distribution line 365(6). Stated differently, in certain embodiments, each of the implant electrodes (i.e., 128(1)-128(22), 140(1), 140(2)) has a single associated switch 355 in the sparse switch network 325 that selectively electrically connects the corresponding electrode to (or electrically disconnects the corresponding electrode from) one and only one of the current sources 326(1)-326(6).

As shown, there are five current sources 326(1)-326(5) that can be connected to the intra-cochlear electrodes 128(1)-128(22), and a sixth current source 326(6) that can be connected to the extra-cochlear electrodes 140(1) and 140(2). Therefore, in the example of FIG. 3, the sparse switch network 325 is further configured such that every fifth intra-cochlear electrode can be connected to the same distribution line 365(1), 365(2), 365(3), 365(4), or 365(5), and thus the same current source 326(1), 326(2), 326(3), 326(4), or 326(5). Stated more generally, there are "M" current sources connectable to the intra-cochlear electrodes 128(1)-128(22) and the sparse switch network 325 is configured to connect every Mth intra-cochlear electrode to the same distribution line and thus the same current source.

The connection of M current sources to every Mth intra-cochlear electrode enables a stimulator unit to deliver current to a recipient in accordance with a number of different stimulation patterns. For example, FIGS. 4A-4E are diagrams illustrating different example stimulation patterns facilitated/enabled by the sparse switch network 325 of FIG. 3. In the examples of FIGS. 4A-4E, the current sources 326(1), 326(2), 326(3), 326(4), 326(5), and 326(6) are represented by the labels S1, S2, S3, S4, S5, and S6, respectively. Similarly, the intra-cochlear electrodes 128(1), 128(2), 128(3), etc. are represented by the respective labels E1, E2, E3, etc., and the extra-cochlear electrodes 140(1) and 140(2) are represented by the labels EE1 and EE2, respectively.

Figure 4A:
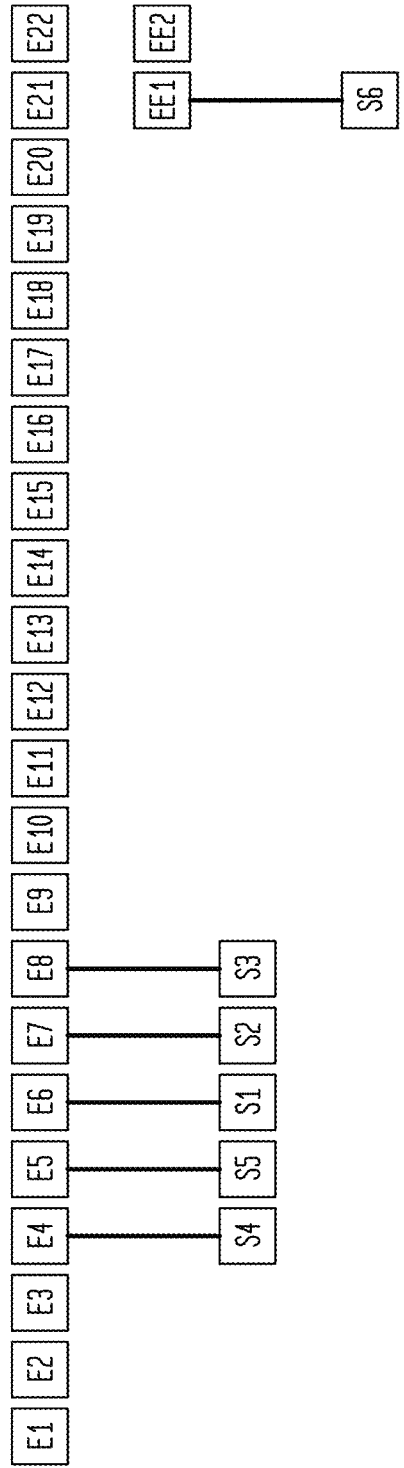
Figure 4B:
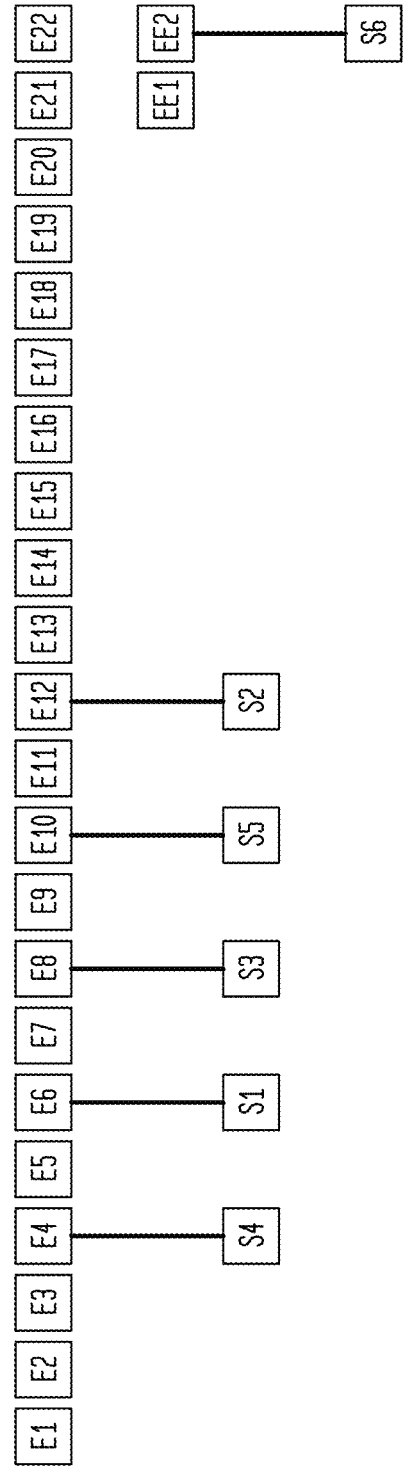

In general, the sparse switch network 325 enables the simultaneous sourcing and/or sinking of stimulation signals (e.g., sourcing and/or sinking current) via any M (i.e., 5) or less sequential stimulation points (intra-cochlear electrodes) with zero to three inactive electrodes between the sequential stimulation points. For example, FIG. 4A illustrates an example in which stimulation is simultaneously sourced/sunk via five consecutive electrodes (i.e., no inactive electrodes between each stimulation point), with current also sourced or sunk at an extra-cochlear electrode. FIGS. 4B and 4C each illustrate examples in which stimulation is simultaneously sourced/sunk via electrodes that are each separated from one another by one inactive electrode (i.e., there is one inactive electrodes between each stimulation point), with current also sourced or sunk at an extra-cochlear electrode. The examples of FIGS. 4B and 4C differ from one another in that different electrodes are used in each example to source/sink the current. Accordingly, FIGS. 4B and 4C illustrate different stimulation locations within a cochlea of a recipient.

Figure 4E:
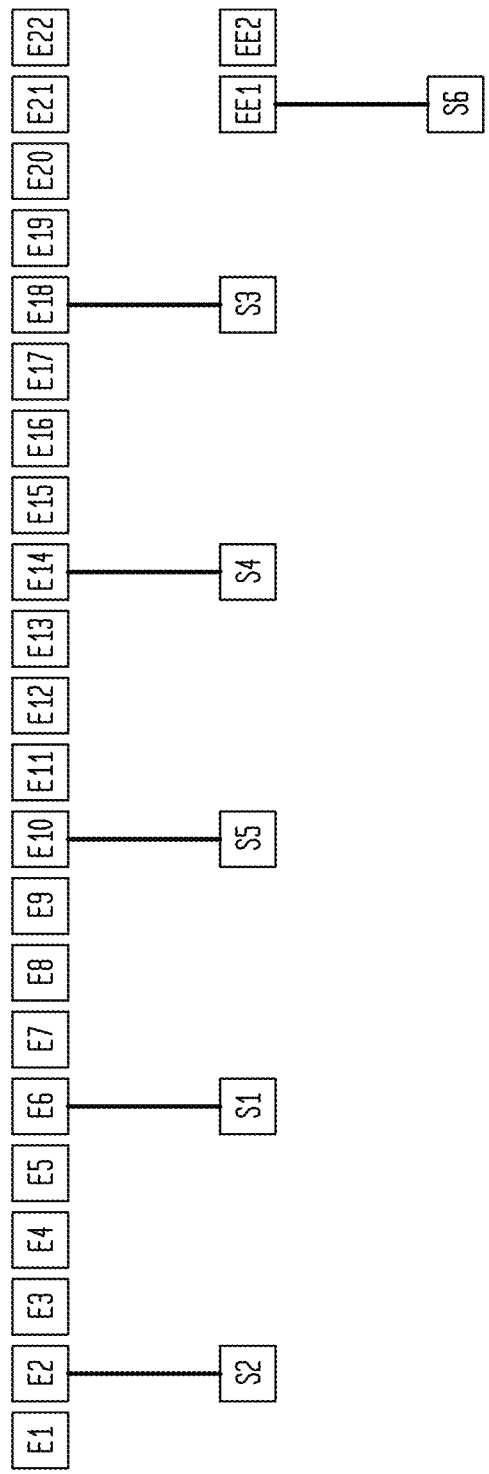

FIG. 4D illustrates an example in which stimulation is simultaneously sourced/sunk via electrodes that are each separated from one another by two inactive electrodes (i.e., there are two inactive electrodes between each stimulation point), and no current is sourced or sunk at an extra-cochlear electrode. FIG. 4E illustrates an example in which stimulation is simultaneously sourced/sunk via electrodes that are each separated from one another by three inactive electrodes (i.e., there are three inactive electrodes between each stimulation point), with current also sourced or sunk at an extra-cochlear electrode.

As noted above, the stimulation patterns shown in FIGS. 4A-4E are illustrative and other stimulation patterns are possible. In certain arrangements, the stimulation patterns may depend on the value of M (i.e., the number of current sources connectable to the intra-cochlear contacts). For example, if M is an odd number, a sparse switch network in accordance with embodiments presented herein can enable stimulation at every second electrode for 2M−1 consecutive electrodes. If M is an odd prime number, the sparse switch network allows for stimulation on M out of KM−X+1 consecutive electrodes with X−1 inactive electrodes between each stimulation point, where X is a natural number.

FIGS. 3 and 4A-4E generally illustrate an arrangement in which there are M+1 current sources in a stimulator unit, where the "M" current sources are selectively connectable to the intra-cochlear electrodes and the additional current source (i.e., the "+1" current source) is selectively connectable to the extra-cochlear electrodes. FIG. 5 is a schematic diagram illustrating one alternative embodiment that provides increased flexibility though the use of M+2 current sources.

More specifically, FIG. 5 illustrates one embodiment of stimulator unit 124, referred to herein as stimulator unit 524, which includes seven current sources 526(1)-526(7) and a sparse switch network 525. The sparse switch network 525 is formed by a plurality of switching elements (switches) 555 that operate under the control of a control unit (controller) 560. Similar to the arrangement of FIG. 3, connections between the switches 555 and the controller 560 have been omitted from FIG. 5 for ease of illustration and it is to be appreciated that the presence of controller 560 in the stimulator unit 524 is illustrative (i.e., the switches 555 may be controlled/actuated by a separate controller, such as an implant controller).

The stimulator unit 524 is shown with the extra-cochlear electrodes 140(1) and 140(2), as well as the electrode array 150 of FIGS. 1A-1C and 2. The intra-cochlear electrodes 128(1)-128(22) of the electrode array 150 are electrically connected to the sparse switch network 525 via a corresponding wire 129(1)-129(22). Similarly, the extra-cochlear electrodes 140(1) and 140(2) are connected to the sparse switch network 525 via wires 129(23) and 129(24), respectively.

In accordance with embodiments presented herein, the sparse switch network 525 is configured to selectively connect each of the current sources 526(1)-526(5) to a plurality (i.e., more than one) of the intra-cochlear electrodes 128(1)-128(22) at different times, and connect each of the intra-cochlear electrodes 128(1)-128(22) to only a subset of the current sources 526(1)-526(5). In addition, the sparse switch network 525 is configured to selectively connect the current source 526(1) to the extra-cochlear electrode 140(1) and/or the extra-cochlear electrode 140(2). In other words, the sparse switch network 525 is a hardwired electrical network that connects each of the current sources 526(1)-526(6) to only a subset of the implanted electrodes (i.e., electrodes 128(1)-128(22), 140(1), or 140(2)). The plurality of switches 555 are arranged to prevent adjacent intra-cochlear electrodes 128(1)-128(22) from being connected to the same current source 526(1)-526(5).

As shown in FIG. 5, each of the current sources 526(1)-526(6) is connected to a corresponding distribution line 565(1)-565(6). In certain embodiments, the sparse switch network 525 is arranged such that each intra-cochlear electrode 128(1)-128(22) can be connected to one and only one of the distribution lines 565(1)-565(5), while the extra-cochlear electrodes 140(1) and 140(2) can each be connected to the distribution line 565(6). Stated differently, in certain embodiments, each of the implanted electrodes (i.e., electrodes 128(1)-128(22), 140(1), and 140(2)) has an associated switch 555 in the sparse switch network 525 that selectively electrically connects the corresponding electrode to (or electrically disconnects the corresponding electrode from) one and only one of the current sources 526(1)-526(6).

As noted, the stimulator unit 524 also comprises a seventh current source 526(7), sometimes referred to herein as an auxiliary current source that can be selectively connected to any of the implant electrodes (i.e., electrodes 128(1)-128(22), 140(1), or 140(2)). More specifically, the sparse switch network 525 includes a seventh distribution line 565(7), sometimes referred to herein as a supplemental or auxiliary distribution line, to which each of the implant electrodes can be electrically connected. Stated differently, each of the implanted electrodes (i.e., electrodes 128(1)-128(22), 140(1), and 140(2)) has an associated primary switch 555 that electrically connects the electrode to one of the current sources 526(1)-526(6), as well as an associated auxiliary switch 555 in the sparse switch network 525 that selectively electrically connects the corresponding electrode to (or electrically disconnects the corresponding electrode from) the auxiliary distribution line 565(7), and thus the current source 526(7).

In the arrangement of FIG. 5, the current sources 526(1)-526(6) are referred to herein as "primary" current sources, while, as noted, the current source 526(7) is sometimes referred to as an "auxiliary" current source. The plurality of switches 555 in the sparse switch network 525 are arranged to selectively connect each of the plurality of the implant electrodes to only one of the primary current sources 526(1)-526(6) and to selectively connect all of the implant electrodes to the auxiliary current source 526(7).

In summary, the sparse switch network 525 of FIG. 5 includes two switches 555 associated with each of the implant electrodes 128(1)-128(22), 140(1), and 140(2). A first one of the two switches 555 associated with an electrode enables the respective electrode to be selectively connected to one and only one of the primary current sources 526(1)-526(6), while the second one of the two switches 555 associated with an electrode enables the respective electrode to be selectively connected to only the auxiliary current source 526(7). The ability to connect any of the electrodes 128(1)-128(22), 140(1), and 140(2) to the auxiliary current source 526(7) increases stimulation flexibility over the arrangement shown in FIG. 3.

The above embodiments have been described with reference to sparse switch networks comprised of "switching elements" or "switches." As used herein, the terms "switching elements" and "switches" are to be broadly construed to include any elements that can be controlled to selectively create/form and terminate/break an electrical connection. For example, as used herein, the terms "switching elements" and "switches" should be construed to include low-impedance floating switches, hi-side/low-side (dual-path) switches, and other circuit elements.

Figure 6:
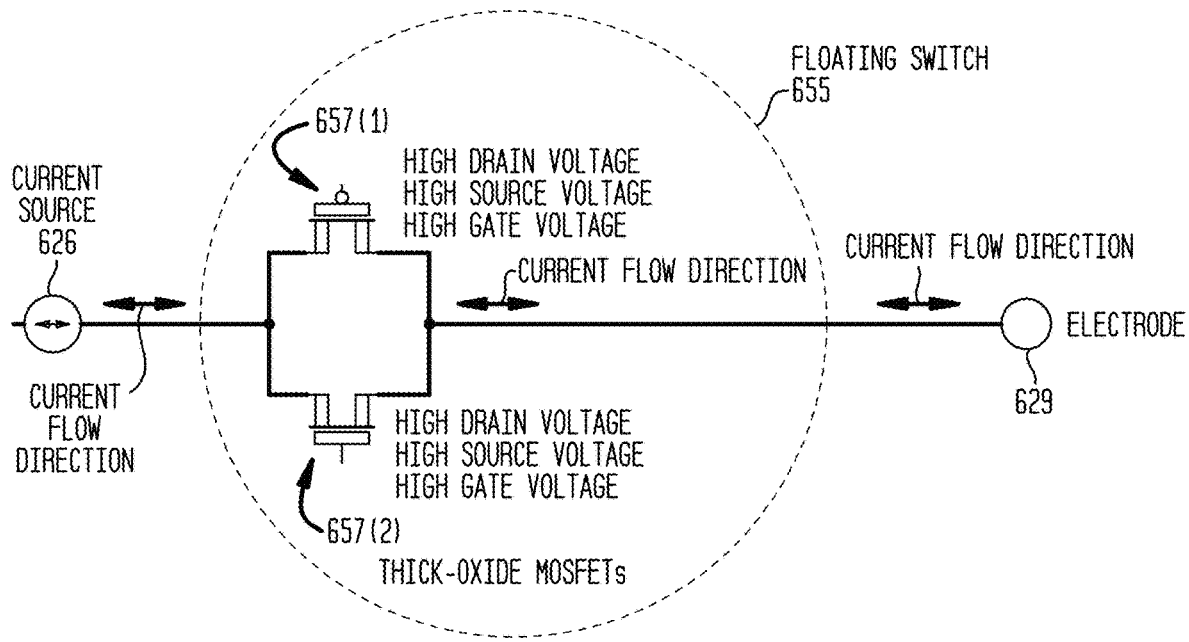
FIG. 6 is a schematic diagram illustrating one type of switch that may form part of a sparse switch network, in accordance with embodiments presented herein.

FIG. 6 is a schematic diagram illustrating an example floating switch 655 that may form part of a sparse switch network in accordance with embodiments presented herein. As shown, the example floating switch 655 is formed by two (2) thick-oxide metal-oxide semiconductor field-effect transistors (MOSFETs) 657(1) and 657(2) that, as part of a sparse switch network, selectively connect a current source 626 to an electrode 629.

Figure 7:
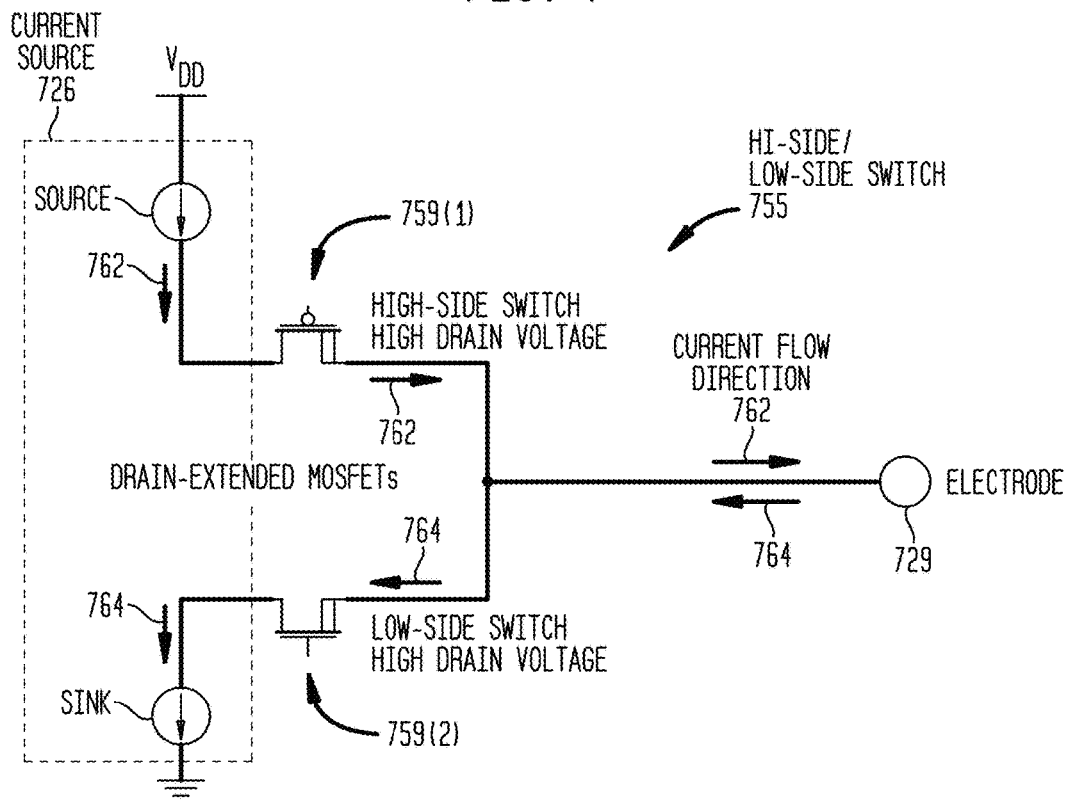
FIG. 7 is a schematic diagram illustrating another type of switch that may form part of a sparse switch network, in accordance with embodiments presented herein.

FIG. 7 is a schematic diagram illustrating an example hi-side/low-side switch 755 that may form part of a sparse switch network in accordance with embodiments presented herein. As shown, the example hi-side/low-side switch 755 is formed by two drain-extended MOSFETs 659(1) and 659(2) that, as part of a sparse switch network, are configured to selectively connect a current source 726 to an electrode 729. FIG. 7 illustrates an arrangement in the current sourced and sunk via separate wires. Therefore, in this embodiment, when current is being sourced via electrode 729, MOSFET 759(1) is closed (conducting) and current flows in the direction shown by arrows 762. When current is being sunk via electrode 729, MOSFET 759(2) is closed (conducting) and current flows in the direction shown by arrows 764. That is, in FIG. 7, a first side of the switch 755 is used to deliver current, while the second side of the switch 755 is used to sink current. The use of a hi-side/low-side switch 755, sometimes referred to as dual-path switch, may be advantageous as these types of switches consume less IC area than, for example, a floating switch.

It is to be appreciated that the examples of FIGS. 6 and 7 are merely illustrative and that other types of switches/switching elements may also or alternatively be used in sparse switch networks presented herein. It is also to be appreciated by a person skilled in the art that the above description describes the core architecture for sparse switch networks in accordance with embodiments of the present invention and that other variations are within the scope of the present invention. For instance, each electrode point in a sparse switch network may have additional switches for connection of measurement devices or for engaging post-stimulation electrode shorting. It is also understood that each stimulator may have two physical distribution lines/wires (one for sinking currents and one for sourcing current) such that the use of low-impedance floating switches can be avoided. Such an arrangement is described below with reference to FIG. 8.

Figure 8:
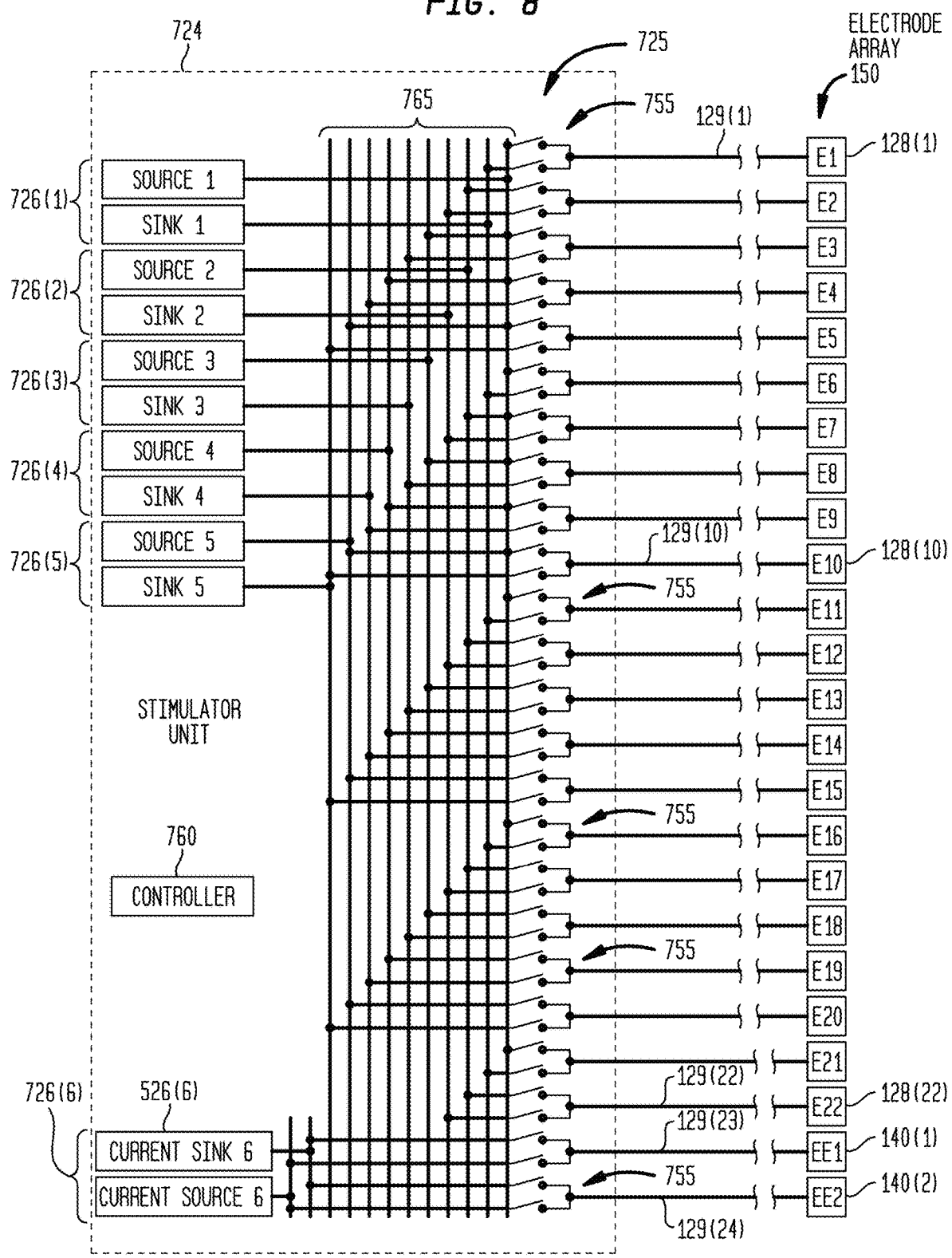
FIG. 8 is a schematic diagram illustrating another stimulator unit having a sparse switch network, in accordance with embodiments presented herein.

FIG. 8 illustrates one embodiment of stimulator unit 124, referred to herein as stimulator unit 724, which makes use of the elements shown in FIG. 7. For ease of explanation, the stimulator unit 724 is shown with the extra-cochlear electrodes 140(1) and 140(2), as well as the electrode array 150 of FIGS. 1A-1C and 2.

As shown, the stimulator unit 724 comprises six current sources 726(1)-726(6) and a sparse switch network 725. The sparse switch network 725 is formed by a plurality of hi-side/low-side switches 755 (as described in FIG. 7) and a plurality of distribution lines 765. Each of the current sources 726(1)-726(6) is arranged such that the current is sourced and sunk via different distribution lines 765 of the sparse switch network 725 (i.e., each current source 726(1)-726(6) has two physical distribution lines/wires 765 associated therewith, one for sinking currents and one for sourcing current). Both of the distribution lines 765 connected to the same current source 726(1)-726(6) are selectively connectable to an electrode via the same hi-side/low-side switch 755. For example, as shown in FIG. 8, the two distribution lines 765 associated with 726(1) are each connectable to electrode 128(1) (i.e., to wire 129(1)) via a single hi-side/low-side switch 755. These two distribution lines 765 associated with 726(1) are also connectable to other electrodes (e.g., electrodes 128(6), 128(11), 128(16), and 128(21)) via other single hi-side/low-side switches 755

In general, the hi-side/low-side switches 755 operate under the control of a control unit, such (controller) 760, an implant controller, etc., to selectively connect each of the current sources 726(1)-726(5) to a plurality (i.e., more than one) of the intra-cochlear electrodes 128(1)-128(22) at different times, and connect each of the intra-cochlear electrodes 128(1)-128(22) to only a subset of the current sources 726(1)-726(5). In addition, the sparse switch network 725 is configured to selectively connect the current source 726(6) to the extra-cochlear electrode 140(1) and/or the extra-cochlear electrode 140(2)). In other words, the sparse switch network 525 is a hardwired electrical network that connects each of the current sources 726(1)-726(6) to only a subset of the implanted electrodes (i.e., electrodes 128(1)-128(22), 140(1), or 140(2)). The plurality of switches 555 are arranged to prevent adjacent intra-cochlear electrodes 128(1)-128(22) from being connected to the same current source 726(1)-726(1). When connected to an electrode, the current sources 726(1)-726(6) may each source or sink current via one of the two associated distribution lines 765.

The design of stimulating devices is typically driven by a desire to provide maximum flexibility in the available stimulation strategies (e.g., stimulate via all of the electrodes at any instance). The embodiments presented herein are orthogonal to these typical design choices. In particular, the embodiments presented herein intentionally reduce stimulation flexibility in order to reduce hardware size/cost. The embodiments presented herein provide an effective use of hardware resources to achieve simultaneous stimulation capabilities, by both limiting the number of current sources and simultaneously restricting the size of the switching network. As a result, the techniques presented herein enable the design of ICs at a reduced size, relative to conventional ICs based on a one-to-one architecture, (translating into reduced implant volume), yet still provide simultaneous functionality. In addition, the techniques presented herein can reduce implant power requirements through a reduction in the number of current sources and/or switches.

FIGS. 1A-8 generally illustrate the use of sparse switch networks with one-dimensional (linear) electrode arrays. It is to be appreciated that sparse switch networks in accordance with embodiments of the present invention may also be used with two-dimensional electrode arrays. Two-dimensional electrode arrays may be used in, for example, brain stem stimulators, vision prostheses, etc.

In a sparse switch network used with a two-dimensional electrode array, a stimulator unit comprises a plurality of stimulators that are arranged into "K" groups (i.e., groups 1, 2, 3, . . . K). Each of the "K" groups of stimulators includes "$M_k$" stimulators, where "k" is an integer from 1 to K. The different K groups of stimulators may include the same or different number of stimulators (i.e., $M_k$ may or may not equal M). As described further below, a sparse switch network used with a two-dimensional electrode array is configured such that each group of stimulators is able to service every K-th row of electrodes in the same fashion as in a one-dimensional array.

A two-dimensional electrode array includes "J" rows of electrodes. Each of these "J" rows includes "$N_j$" electrodes, where j is an integer from 1 to J. Again, it is not necessary that all rows of electrodes have the same number of electrodes, but it is possible to set $N_j=N$. For proper hardware saving, it is assumed that the number of electrodes in each row is larger than the number of stimulators serving that row (i.e., $N_j>M_k$ or possibly $N_j>>M_k$) and that the number of rows is larger than the number of stimulator groups (i.e., J>K or possibly J>>K).

Figure 9:
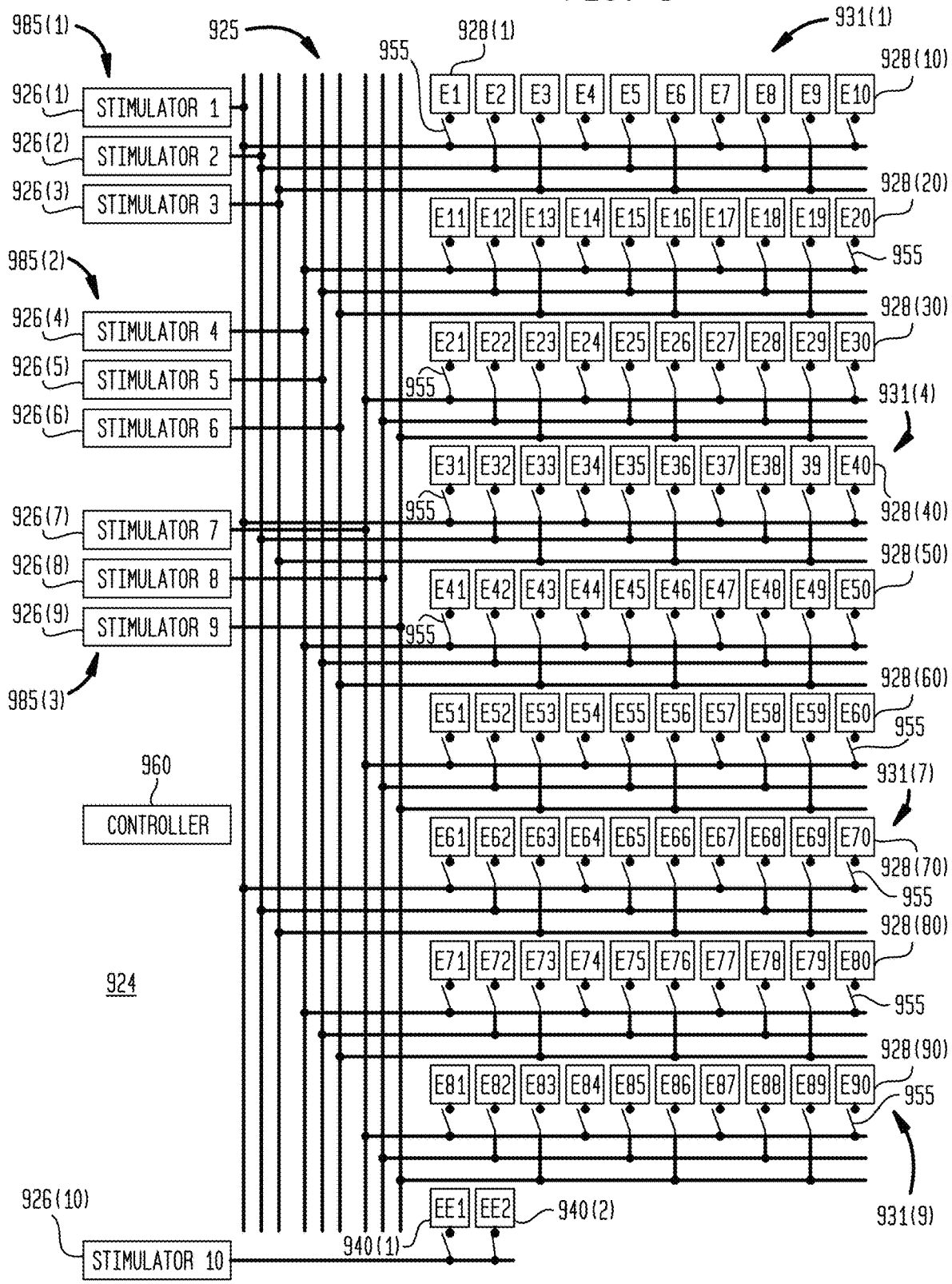
FIG. 9 is a schematic diagram illustrating a stimulator unit having a sparse switch network, in accordance with embodiments presented herein.
Figure 10A:
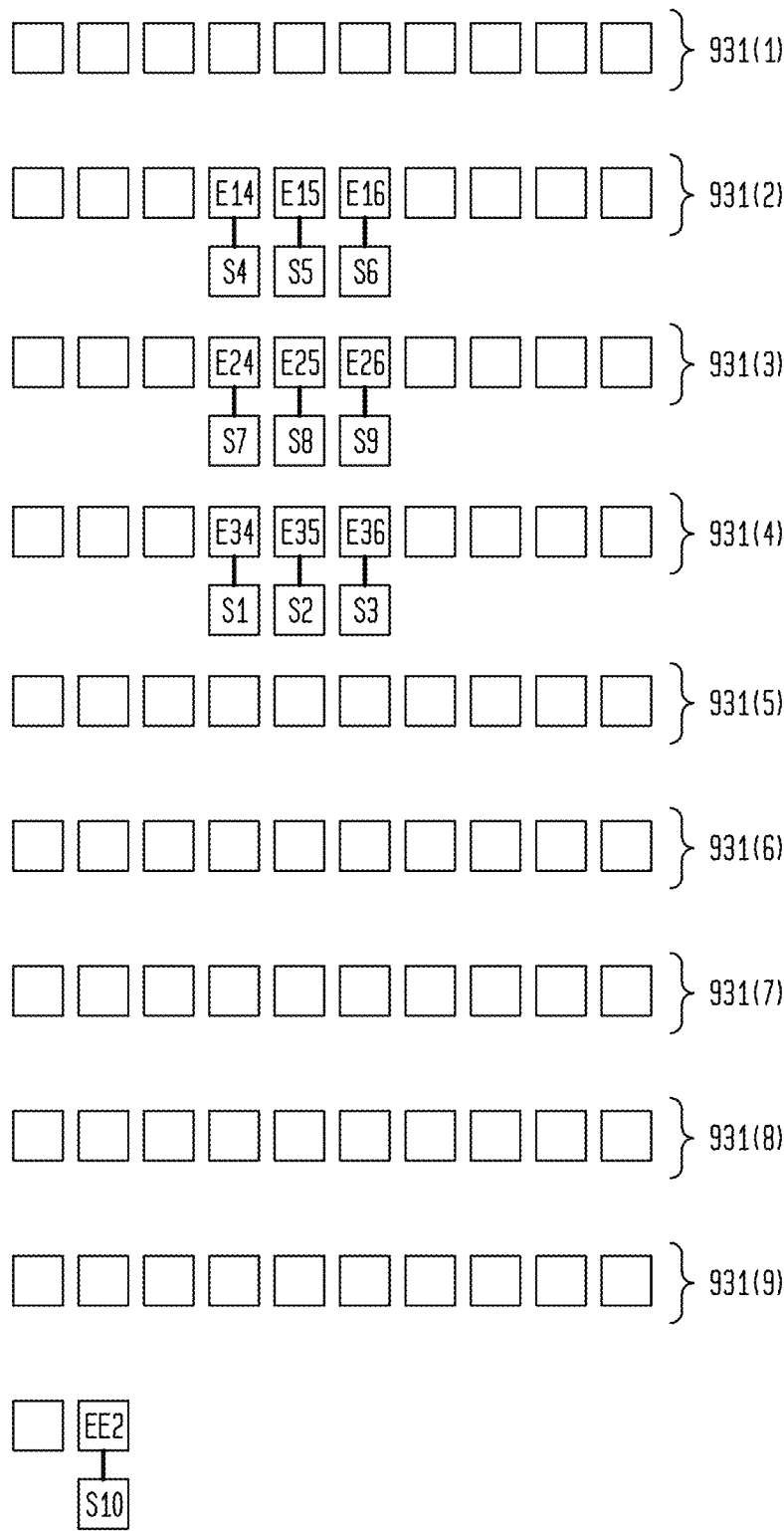
FIGS. 10A, 10B, 10C, and 10D are diagrams illustrating different example stimulation patterns facilitated/enabled by sparse switch network, in accordance with embodiments presented herein.
Figure 10B:
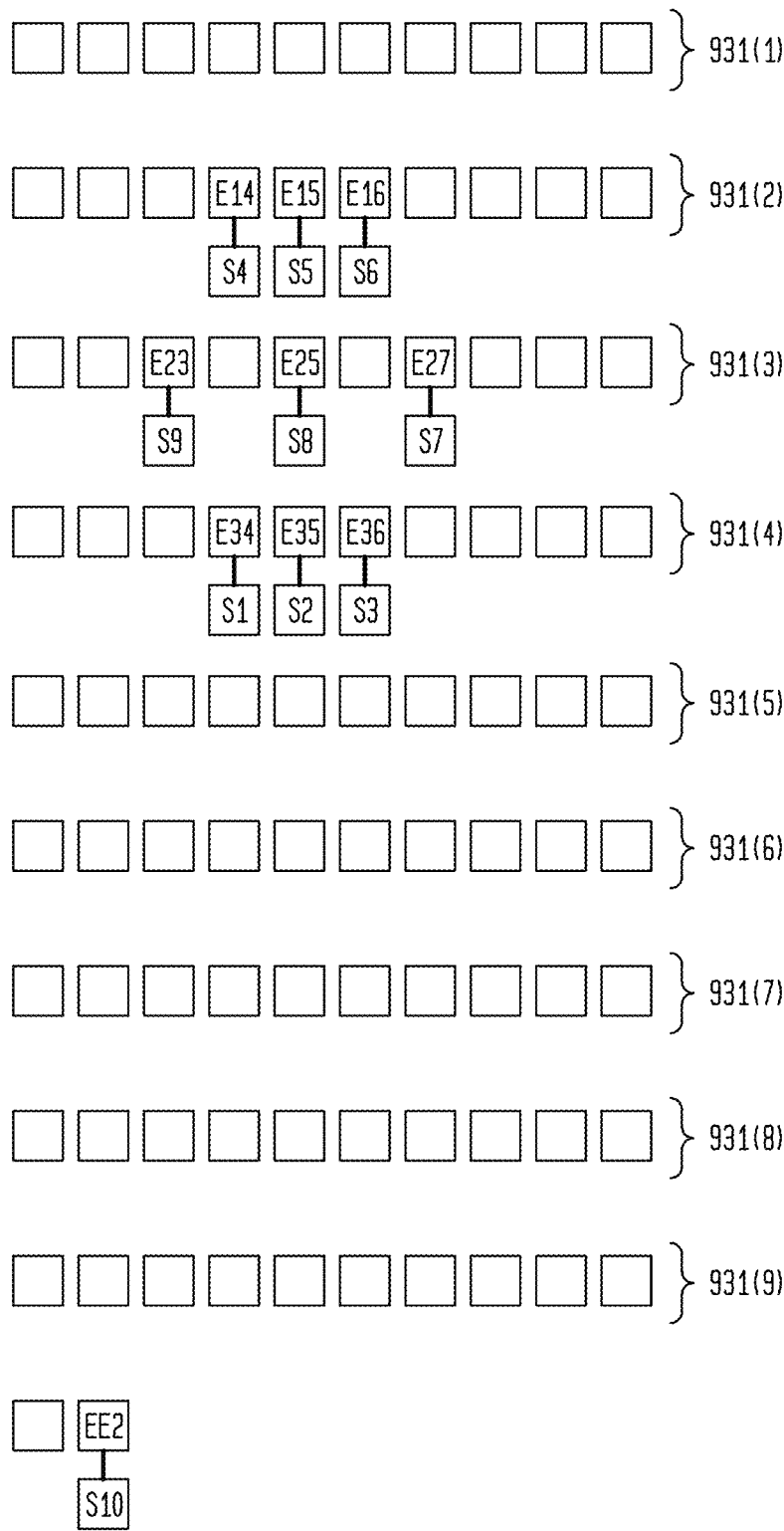
Figure 10C:
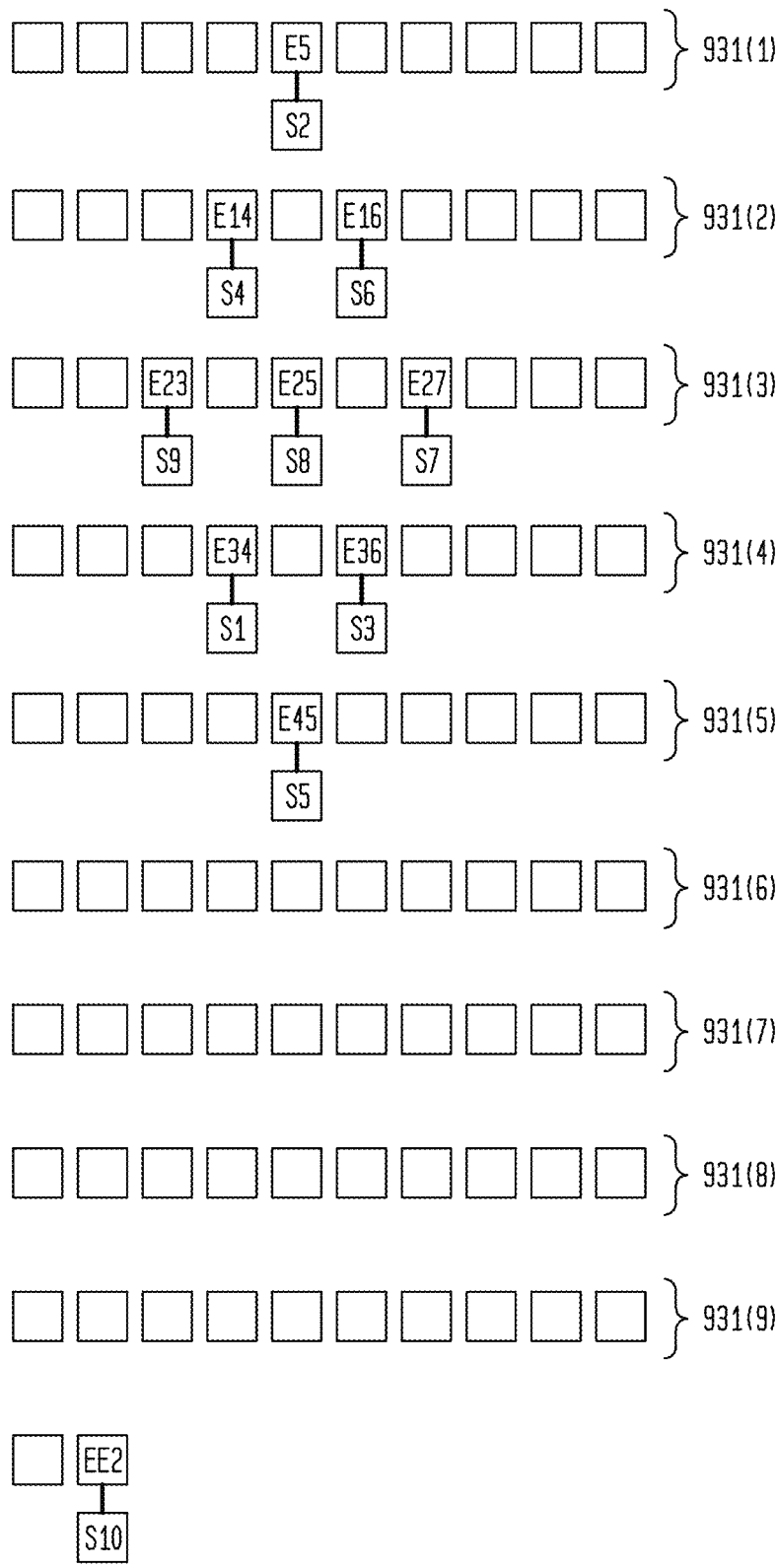
Figure 10D:
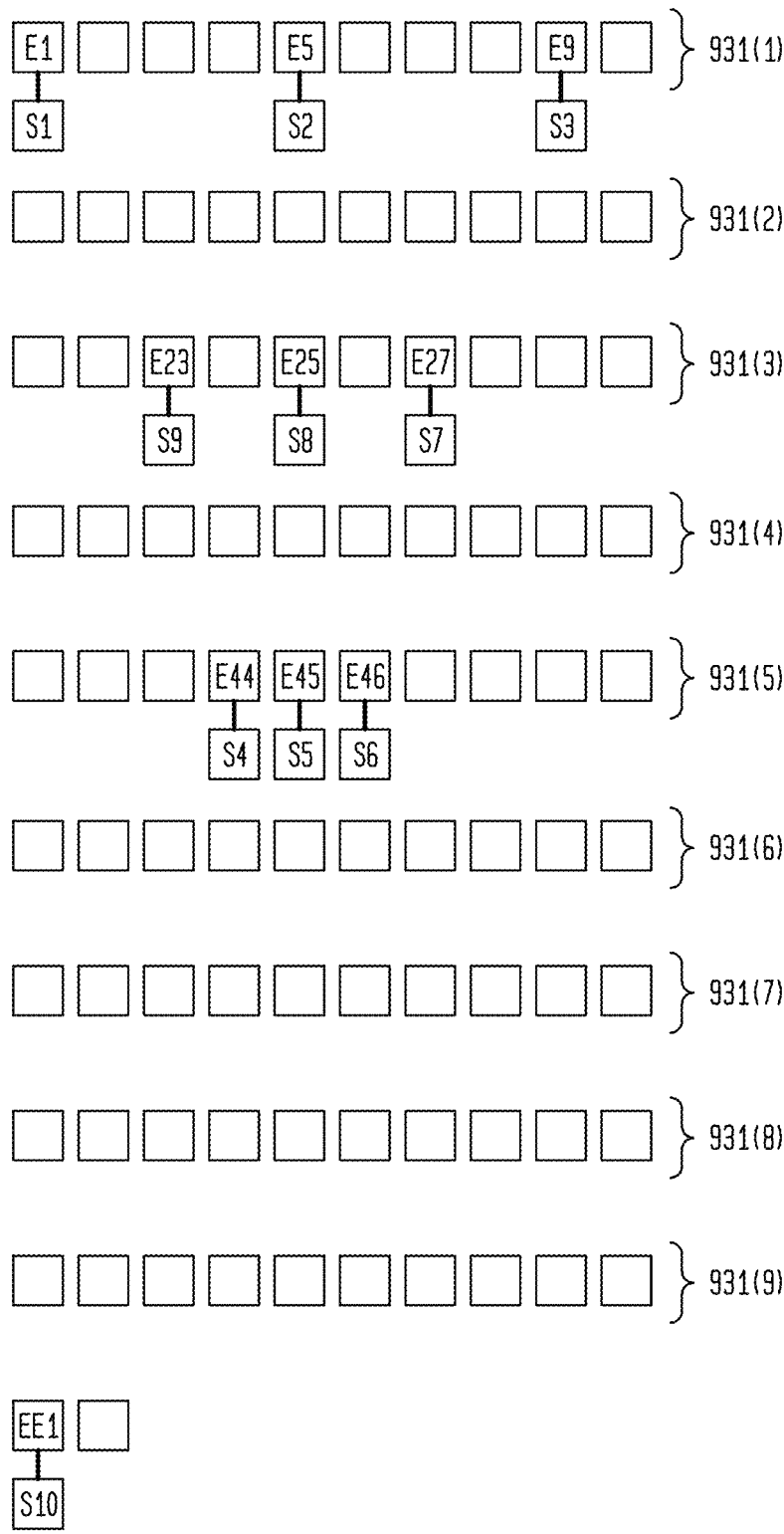

FIG. 9 is a schematic diagram illustrating a stimulator unit 924 that comprises ten (10) stimulators 926(1)-926(10) and a sparse switch network 925 in accordance with embodiments presented herein. The sparse switch network 925 is configured to selectively connect the stimulators 926(1)-926(10) to a two-dimensional electrode array 950.

The sparse switch network 925 is formed by a plurality of switching elements (switches) 955 that operate under the control of a control unit (controller) 960. For ease of illustration, connections between the switches 955 and the controller 960 have been omitted from FIG. 9. Although FIG. 9 illustrates the presence of a controller 960 that forms part of stimulator unit 924, it is to be appreciated that this is merely illustrative and that switches 955 may be controlled/actuated by a separate controller.

In this example, the electrode array 950 comprises ninety (90) electrodes 928(1)-928(90) that are organized into a plurality of different rows/lines 931(1)-931(9) that each include 10 electrodes. Also shown in FIG. 9 are two reference electrodes 940(1) and 940(2). In example of FIG. 9, there are three groups of stimulators (i.e., K=3), referred to as groups 985(1), 985(2), and 985(3). Each of these three groups includes three stimulators (i.e., $M_k=3$ and $M_k=M$). As noted, there are nine rows 931(1)-939(9) of electrodes (i.e., J=9), where each row includes 10 electrodes (i.e., $N_j=10$ and $N_j=N$). There is also an extra stimulator 926(1) serving the two reference electrodes 940(1) and 940(2).

In accordance with embodiments presented herein, the sparse switch network 925 is configured to selectively connect each of the current sources 926(1)-926(9) to a plurality (i.e., more than one) of the electrodes 928(1)-928(90) at different times, and to selectively connect each of the electrodes 928(1)-928(90) to only a subset of the current sources 926(1)-926(9). In addition, the sparse switch network 925 is configured to selectively connect the current source 926(10) to the reference electrode 940(1) and/or the reference electrode 940(2). In other words, the sparse switch network 925 is a hardwired electrical network comprised of a plurality of switches 955 that is configured to selectively connect, at different times, each of the current sources 926(1)-926(10) to only a subset of the implanted electrodes (i.e., electrodes 928(1)-928(90), 940(1), or 940(2)).

More specifically, in the example of FIG. 9, the sparse switch network 925 is configured such that each group 985(1), 985(2), and 985(3) of stimulators is able to service every third row of electrodes in the same fashion as in a one-dimensional array. For example, stimulators 926(1), 926(2), and 926(3) form stimulator group 985(1), stimulators 926(4), 926(5), and 926(6) form stimulator group 985(2), and stimulators 926(7), 926(8), and 926(9) form stimulator group 985(3). The sparse switch network 925 is configured such that the stimulators in group 985(1) are selectively connectable to the electrodes in lines 931(1), 931(4), and 931(7), while the stimulators in group 985(2) are selectively connectable to the electrodes in lines 931(2), 931(5), and 931(8) (i.e., every $3^{rd}$ row of electrodes) The stimulators in group 985(3) are selectively connectable to the electrodes in lines 931(3), 931(6), and 931(9).

The sparse switch network 925 of FIG. 9 enables the delivery of current to a recipient in accordance with a number of different stimulation patterns. For example, FIGS. 10A-10D are diagrams illustrating different example stimulation patterns facilitated/enabled by the sparse switch network 925 of FIG. 9. In the examples of FIGS. 10A-10D, the current sources 926(1), 926(2), 926(3), 926(4), 926(5), 926(6), 926(7), 926(8), 926(9), and 926(10) are represented by the labels S1, S2, S3, S4, S5, S6, S7, S8, S9, and S10, respectively. Similarly, the electrodes 928(1), 928(2), 928(3), etc. are represented by the respective labels E1, E2, E3, etc., and the reference electrodes 940(1) and 940(2) are represented by the labels EE1 and EE2, respectively.

In general, the examples of FIGS. 10A-10D, when looking at individual rows have similar possibilities as for a one-dimensional array. Each of the rows 931(1)-939(9) can be serviced in the same patterns as electrodes within a one-dimensional array (e.g., any K consecutive rows, every second row for 2K+1 rows, etc.). However, as shown, additional flexibility is added in that stimulators in one group do not have to all service the same row.

For ease of illustration, FIG. 9 illustrates a rectangular two-dimensional array 950. It is to be appreciated that a sparse stimulation network in accordance with embodiments presented herein may also be used with two-dimensional arrays that have other shapes (e.g., square, hexagonal arrays, etc.) and that the use of a rectangular two-dimensional array is illustrative.

Merely for ease of illustration, the embodiments presented herein are primarily described herein with reference to one type of tissue-stimulating prosthesis, namely a cochlear implant. However, it is to be appreciated that the techniques presented herein may be used with other tissue-stimulating prostheses including, for example, auditory brainstem stimulators, implantable pacemakers, defibrillators, functional electrical stimulation devices, pain relief stimulators, visual prostheses, other neural or neuromuscular stimulators, etc.

It is to be appreciated that the above embodiments are not mutually exclusive and may be combined with one another in various arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An implantable medical device, comprising:
   current sources configured to generate stimulation signals for delivery to a recipient of the implantable medical device;
   an array of stimulating electrodes; and
   a plurality of switches configured to selectively electrically connect each of a plurality of the current sources to a plurality of the stimulating electrodes,
   wherein the plurality of switches is arranged to prevent adjacent stimulating electrodes from being connected to a same one of the plurality of current sources and wherein the plurality of switches is arranged to connect each of the stimulating electrodes to only two of the plurality of current sources.

2. The implantable medical device of claim 1, wherein the plurality of switches is arranged to selectively connect each of the stimulating electrodes to only a subset of the plurality of current sources, and arranged to selectively connect each of the plurality of current sources to only a subset of the stimulating electrodes.

3. The implantable medical device of claim 1, wherein the plurality of switches is arranged to prevent a connection between each of the stimulating electrodes and at least one of the plurality of current sources.

4. The implantable medical device of claim 1, wherein the plurality of switches is arranged to concurrently connect a subset of the stimulating electrodes to at least a subset of the plurality of current sources, and wherein the subset of the stimulating electrodes comprises a group of sequential stimulating electrodes from the array.

5. The implantable medical device of claim 1, wherein each of the stimulating electrodes is connected to a single one of the plurality of switches.

6. The implantable medical device of claim 1, wherein the plurality of switches has a hardwired pattern between the plurality of current sources and the stimulating electrodes.

7. The implantable medical device of claim 1, wherein:
each of the stimulating electrodes is connected to a single one of the plurality of current sources via one of the plurality of switches, and
the plurality of current sources are connected sequentially to the stimulating electrodes in the array, wherein a connection sequence repeats along the array.

8. The implantable medical device of claim 1, wherein each switch of the plurality of switches is a hi-side/low-side switch.

9. A tissue-stimulating prosthesis, comprising:
a plurality of electrodes;
a plurality of current sources; and
a sparse switch network configured to: (i) connect each of the current sources to more than one of the electrodes, and (ii) connect each of the electrodes to only a subset of the current sources,
wherein the plurality of current sources comprise a plurality of primary current sources and at least one auxiliary current source, and wherein the sparse switch network is configured to selectively connect each of the plurality of electrodes to only one of the primary current sources and to selectively connect all of the electrodes to the at least one auxiliary current source.

10. The tissue-stimulating prosthesis of claim 9, wherein the sparse switch network comprises a plurality of switches, and wherein each of the switches connects one of the electrodes to one of the primary current sources.

11. The tissue-stimulating prosthesis of claim 9, wherein the number of primary current sources is less than the number of electrodes.

12. The tissue-stimulating prosthesis of claim 9, wherein the at least one auxiliary current source comprises a plurality of auxiliary current sources.

13. The tissue-stimulating prosthesis of claim 9, wherein the sparse switch network comprises a plurality of switches have a hardwired pattern between the plurality of current sources and the electrodes.

14. The tissue-stimulating prosthesis of claim 9, wherein the plurality of electrodes is disposed in a linear array.

15. The tissue-stimulating prosthesis of claim 9, wherein the plurality of electrodes is disposed in a two-dimensional.

16. The tissue-stimulating prosthesis of claim 9, wherein the plurality of switches is arranged to prevent a connection between each of the electrodes and at least one of the plurality of current sources.

17. A tissue-stimulating prosthesis, comprising:
a plurality of current sources, wherein each of the current sources is configured to produce an electrical stimulation signal; and
an array of stimulating electrodes, wherein the stimulating electrodes are configured to deliver electrical stimulation signals received from the current sources to tissue of a recipient; and
a hardwired electrical network that connects each of the current sources to only a subset of the stimulating electrodes,
wherein the plurality of current sources comprises a plurality of primary current sources and at least one auxiliary current source, and wherein the hardwired electrical network is configured to selectively connect each of the stimulating electrodes to only one of the primary current sources and to selectively connect all of the stimulating electrodes to the at least one auxiliary current source.

18. The tissue-stimulating prosthesis of claim 17, wherein:
the hardwired electrical network comprises a plurality of switches, and
each of the switches connects one of the stimulating electrodes to only one of the plurality of primary current sources.

19. The tissue-stimulating prosthesis of claim 17, wherein the hardwired electrical network connects each of the plurality of primary current sources to more than one of the stimulating electrodes.

20. The tissue-stimulating prosthesis of claim 17, wherein the hardwired electrical network is configured to decouple adjacent stimulating electrodes from a same one of the plurality of primary current sources.

21. The tissue-stimulating prosthesis of claim 17, wherein the hardwired electrical network is configured to prevent a connection between each of the stimulating electrodes and at least one of the plurality of primary current sources.

22. The tissue-stimulating prosthesis of claim 17, wherein the at least one auxiliary current source comprises a plurality of auxiliary current sources.

23. The tissue-stimulating prosthesis of claim 17, wherein the hardwired electrical network is configured to enable a simultaneously delivery of electrical stimulation signals from two or more of the plurality of primary current sources to sequential stimulating electrodes of the array.

* * * * *